(12) United States Patent
Kellar et al.

(10) Patent No.: US 10,293,080 B2
(45) Date of Patent: May 21, 2019

(54) IONIC LIQUIDS THAT STERILIZE AND PREVENT BIOFILM FORMATION IN SKIN WOUND HEALING DEVICES

(71) Applicants: The Arizona Board of Regents on Behalf of Northern Arizona University, Flagstaff, AZ (US); Dixie State University, St. George, UT (US)

(72) Inventors: Robert Kellar, Flagstaff, AZ (US); Nathan Christopher Nieto, Flagstaff, AZ (US); Andrew Koppisch, Flagstaff, AZ (US); Rico Del Sesto, St. George, UT (US)

(73) Assignees: The Arizona Board of Regents on Behalf of Northern Arizona University, Flagstaff, AZ (US); Dixie State University, St. George, UT (US)

( * ) Notice: Subject to any disclaimer, the term of this patent is extended or adjusted under 35 U.S.C. 154(b) by 0 days.

(21) Appl. No.: 15/725,213

(22) Filed: Oct. 4, 2017

(65) Prior Publication Data
US 2018/0093011 A1 Apr. 5, 2018

Related U.S. Application Data

(60) Provisional application No. 62/404,369, filed on Oct. 5, 2016.

(51) Int. Cl.
| | | |
|---|---|---|
| *A61K 31/14* | (2006.01) | |
| *A61L 26/00* | (2006.01) | |
| *A61K 31/20* | (2006.01) | |
| *A61K 9/00* | (2006.01) | |
| *A61K 38/39* | (2006.01) | |
| *D01D 5/00* | (2006.01) | |
| *D01F 1/10* | (2006.01) | |
| *A61L 15/32* | (2006.01) | |
| *A61L 15/44* | (2006.01) | |

(52) U.S. Cl.
CPC ........ *A61L 26/0038* (2013.01); *A61K 9/0014* (2013.01); *A61K 31/14* (2013.01); *A61K 31/20* (2013.01); *A61K 38/39* (2013.01); *A61L 15/32* (2013.01); *A61L 15/44* (2013.01); *A61L 26/0033* (2013.01); *A61L 26/0042* (2013.01); *D01D 5/003* (2013.01); *D01F 1/103* (2013.01); *A61L 2300/404* (2013.01); *D01D 5/0015* (2013.01)

(58) Field of Classification Search
CPC ..... A61K 31/14; A61L 26/0038; A61L 15/32; D01D 5/0015; D01D 5/003
See application file for complete search history.

(56) References Cited

FOREIGN PATENT DOCUMENTS

| CN | 103554247 A | * | 2/2014 | |
|---|---|---|---|---|
| FR | 2974807 A1 | * | 11/2012 | ............... C08K 5/50 |

OTHER PUBLICATIONS

Translation of CN103554247A abstract, 2014, pp. 1-3 (Year: 2014).*
Docherty, K.M. et al. "Toxicity and antimicrobial activity of imidazolium and pyridinium ionic liquids" Green Chem., 2005, 7, 185-189 (Year: 2005).*
Machine translation of FR2974807A1, 2018, pp. 1-11 (Year: 2018).*
Srivastava et al. "Fabrication of robust Antheraea assama fibroin nanofibrous mat using ionic liquid for skin tissue engineering" Materials Science and Engineering C 68 (2016) 276-290 (Year: 2016).*
Zakrewsky, M. et al. "Ionic liquids as a class of materials for transdermal delivery and pathogen neutralization" PNAS Sep. 16, 2014, vol. 111, No. 37, pp. 13313-13318 (Year: 2014).*
Dongargaonkar, A.A. "Electrospun Blends of Gelatin and Gelatin-Dendrimer Conjugates as a Wound-Dressing and Drug-Delivery Platform" Biomacromolecules 2013, 14, 4038-4045 (Year: 2013).*
Park, T-J. et al. "Native Chitosan/Cellulose Composite Fibers from an Ionic Liquid via Electrospinning" Macromolecular Research, vol. 19, No. 3, pp. 213-215 (2011) (Year: 2011).*
Baumgarten, Electrostatic spinning of acrylic microfibers. *Journal of colloid and interface science* 36.1: 71-79, 1971.
Bickers et al. (2006) The burden of skin diseases: 2004—A joint project of the American Academy of Dermatology Association and the Society for Investigative Dermatology. *J Am Acad Dermatol* 55(3):490-500.
Cao Y, et al., Separation of soybean isoflavone aglycone homologues by ionic liquid-based extraction. *Journal of agricultural and food chemistry* 60(13):3432-3440, 2012.
Davis, S. C., et al. Microscopic and physiologic evidence for biofilm-associated wound colonization in vivo. *Wound Repair and Regeneration*, 2008, 16: 23-29.
De Diego et al., A recyclable enzymatic biodiesel production process in ionic liquids. *Bioresource technology* 102(10):6336-6339, 2012.
Donlan et al. (2001) Biofilms and device-associated infections. *Emerg Infect Dis* 7(2):277-281.
Eisenberg, Ionic interactions in biological and physical systems: a variational treatment. *Faraday discussions* 160:279-296, 2013.
Falanga, V. Wound healing and its impairment in the diabetic foot. *The Lancet*, 366(9498), 1736-1743. 2005.
Flemming et al. (2010) The biofilm matrix. *Nature Reviews Microbiology* 8(9):623-633.
Frederix M, et al., Development of a native *Escherichia coli* induction system for ionic liquid tolerance. *PloS one* 9(7):e101115, 2014.
Garg et al. Electrospinning jets and nanofibrous structures. *Biomicrofluidics* 5.1: 013403, 2011.

(Continued)

*Primary Examiner* — Andrew S Rosenthal
(74) *Attorney, Agent, or Firm* — Knobbe Martens Olson & Bear LLP

(57) ABSTRACT

Compositions for enhancing wound healing are disclosed herein. Also disclosed are methods of making the compositions and methods of using the compositions for the prevention of biofilm formation and for the inhibition of pathogen growth and proliferation.

22 Claims, 25 Drawing Sheets

(56) References Cited

OTHER PUBLICATIONS

Hassan et al., Studies on the dissolution of glucose in ionic liquids and extraction using the antisolvent method. *Environmental science & technology* 47(6):2809-2816, 2013.

Hayati et al., Investigations into the mechanisms of electrohydrodynamic spraying of liquids: I. Effect of electric field and the environment on pendant drops and factors affecting the formation of stable jets and atomization. *Journal of Colloid and Interface Science* 117.1: 205-221, 1987.

Laing et al. (2010). Pan-genome sequence analysis using Panseq: an online tool for the rapid analysis of core and accessory genomic regions. BMC Bioinformatics. 11:461.

Lovejoy, et al. (2011) Tetraalkylphosphonium-Based Ionic Liquids for a Single-Step Dye Extraction/MALDI MS Analysis Platform. *Anal Chem* 83(8):2921-2930.

Lovejoy et al. (2012) Single-Pot Extraction-Analysis of Dyed Wool Fibers with Ionic Liquids. *Anal Chem* 84(21):9169-9175.

Lovejoy et al. (2012) Utilization of Metal Halide Species Ambiguity to Develop Amorphous, Stabilized Pharmaceutical Agents as Ionic Liquids. *Cryst Growth Des* 12(11):5357-5364.

Margolis et al., Incidence of diabetic foot ulcer and lower extremity amputation among Medicare beneficiaries, 2006 to 2008, Data Points Publication Series, Feb. 17, 2011.

Menke, et al., Impaired wound healing. *Clinics in dermatology*, 25(1), 19-25. 2007.

Merritt et al. (2005) Growing and analyzing static biofilms. *Current protocols in microbiology* Chapter 1:Unit 1B 1.

Shill K, et al. (2011) Ionic liquid pretreatment of cellulosic biomass: enzymatic hydrolysis and ionic liquid recycle. *Biotechnology and bioengineering* 108(3):511-520.

Sterodimas, Aris, et al. Tissue engineering with adipose-derived stem cells (ADSCs): current and future applications. *Journal of Plastic, Reconstructive & Aesthetic Surgery* 63.11: 1886-1892, 2010.

Stosich, et al. Adipose tissue engineering from human adult stem cells: clinical implications in plastic and reconstructive surgery. *Plastic and reconstructive surgery* 119.1: 71, 2007.

Taylor. Electrically driven jets. *Proceedings of the Royal Society of London A: Mathematical, Physical and Engineering Sciences*. vol. 313. No. 1515. The Royal Society, 1969.

Uju, et al. (2013) Peracetic acid-ionic liquid pretreatment to enhance enzymatic saccharification of lignocellulosic biomass. *Bioresource technology* 138:87-94.

Varanasi P, et al. (2013) Survey of renewable chemicals produced from lignocellulosic biomass during ionic liquid pretreatment. *Biotechnology for biofuels* 6(1):14.

Wysocki, Annette B. Evaluating and managing open skin wounds: colonization versus infection. *AACN Advanced Critical Care* 13.3: 382-397, 2002.

Yang et al. 2013. Pan-PCR, a Computational Method for Designing Bacterium-Typing Assays Based on Whole-Genome Sequence Data. J. Clin. Microbiol. 51:3 752-758.

Zakrewsky et al. (2014) Ionic liquids as a class of materials for transdermal delivery and pathogen neutralization. *P Natl Acad Sci USA* 111(37):13313-13318.

Zhang J, et al. (2014) Understanding changes in cellulose crystalline structure of lignocellulosic biomass during ionic liquid pretreatment by XRD. *Bioresource technology* 151:402-405.

\* cited by examiner

IONIC LIQUIDS THAT STERILIZE AND PREVENT BIOFILM FORMATION IN SKIN WOUND HEALING DEVICES

CROSS-REFERENCE TO RELATED APPLICATIONS

This application claims the benefit of priority to U.S. Provisional Application No. 62/404,369, filed Oct. 5, 2016, the disclosure of which is hereby expressly incorporated by reference in its entirety.

FIELD

The present disclosure relates generally to the field of wound healing. In particular, the disclosure relates to compositions for enhancing wound healing. Such compositions include an ionic liquid and a protein scaffold. The compositions can be impregnated into a wound healing device, such as a bandage, or dressing. The disclosure also relates to methods of making the compositions and using the compositions to treat wounds.

BACKGROUND

Wound healing is a complex cascade of events that attempts to maintain homeostasis in the wounded tissue. Closing of the wound is essential to the healing process as it protects the tissue itself from infection with foreign agents, such as opportunistic bacterial pathogens. Biofilms established by these pathogens are a common cause of chronic infections that slow the process of wound healing. The bacterial biofilms themselves are challenging to eliminate with conventional antibiotics due to an extensive exopolymeric layer covering the pathogen that limits diffusion of these drugs into the biofilm. Ionic liquids, such including deep eutectic solvents (DESs), is a family of molecules with diverse chemical properties.

When considering dermal wound healing, there is a driving need for the organism to close the wound from the environment as a form of protection. If the wound does not close in a sufficient amount of time, foreign agents can enter the body and have serious pathological effects. Additionally, in a clinical environment, various devices and/or materials are implanted into the integument (skin) to treat the skin or other tissues and organs. In these cases, altering the skin environment can present significant risks to the organism (patient) for bacteria, viral, or fungal contamination of the compromised skin.

A specific patient population at significant risk for open wound contamination by biofilm formation includes unmanaged diabetic patients who develop chronic, non-healing wounds. Diabetic foot ulcers affect an estimated 1.4 million people in the U.S., resulting in enormous health care expenditures estimated at more than $176 billion per year for 2012 (Margolis et al., Incidence of diabetic foot ulcer and lower extremity amputation among Medicare beneficiaries, 2006 to 2008, Data Points Publication Series, Feb. 17, 2011; Mathieu, D. (Ed). *Handbook on hyperbaric medicine* (Vol. 27). New York: Springer. 2006; Menke, et al., Impaired wound healing. *Clinics in dermatology*, 25(1), 19-25. 2007. *Washington health system: Washington hospital.* (2014)). Diabetic patients who have chronic disease may experience persistent wounds for months to years. Furthermore, if healing occurs, the healed tissue has substantial scarring and the scar may fail, resulting in recurrence of the ulcer.

Chronic diabetic wounds pose different pathophysiological abnormalities that contribute to a complex wound microenvironment that varies from the "normal" wound healing cascade (Falanga, V. Wound healing and its impairment in the diabetic foot. *The Lancet*, 366(9498), 1736-1743. 2005). This variation leads to a loss of synchrony of events indicative of rapid healing. There is a pathogenic triad of events that are predisposed in diabetic patients consisting of neuropathy, ischemia and trauma that hinders normal healing. Each of these factors affects each other in a way that results in an impaired ability to fight infection and presents difficulties in closing chronic skin wounds.

Currently, the clinical treatment of full thickness skin wounds presents a significant challenge. Therapies for the treatment of these skin wounds include autologous tissue grafts and fat transplantation (replacing burnt or severely traumatized tissue with a patient's own skin & fat tissue—taken from a distant site), and alloplastic (synthetic) implants. However, these methods present significant problems for the patient including donor site morbidity, implant migration, rupture, volume reduction, and foreign body reaction (Sterodimas, Aris, et al. Tissue engineering with adipose-derived stem cells (ADSCs): current and future applications. *Journal of Plastic, Reconstructive & Aesthetic Surgery* 63.11: 1886-1892, 2010; Stosich, et al. Adipose tissue engineering from human adult stem cells: clinical implications in plastic and reconstructive surgery. *Plastic and reconstructive surgery* 119.1: 71, 2007).

Furthermore, a lack of subcutaneous adipose tissue in full thickness skin wounds contributes to the aesthetically unappealing post-operative appearance (Shill K, et al. (2011) Ionic liquid pretreatment of cellulosic biomass: enzymatic hydrolysis and ionic liquid recycle. *Biotechnology and bioengineering* 108(3):511-520). There remains a major clinical demand for better methods of skin tissue healing of diabetic foot ulcers but also following severe burns, tumor excision, and trauma (Sterodimas, Aris, et al. Tissue engineering with adipose-derived stem cells (ADSCs): current and future applications. *Journal of Plastic, Reconstructive & Aesthetic Surgery* 63.11: 1886-1892, 2010).

In the clinical treatment of wounds, it is well established that open skin wounds colonize with bacteria; therefore, optimized wound care targets rapid wound closure in efforts to prevent infection and possible sepsis in severe cases (Wysocki, Annette B. Evaluating and managing open skin wounds: colonization versus infection. *AACN Advanced Critical Care* 13.3: 382-397, 2002). Today, wound care to prevent progression from colonization to infection remains the paramount objective of health care providers. However, this progression has become progressively difficult to combat due to emergent antimicrobial resistance (Davis, S. C., et al. Microscopic and physiologic evidence for biofilm-associated wound colonization in vivo. *Wound Repair and Regeneration*, 2008, 16: 23-29).

SUMMARY

The present disclosure generally relates to wound care compositions and methods of making and using the same.

Accordingly, in some embodiments is provided a wound care composition including an ionic liquid and a protein scaffold. In some embodiments, the wound care composition is formulated for incorporation into a wound dressing, a bandage, gauze, a patch, a pad, tape, or a wrap.

In some embodiments, the wound care composition includes an ionic liquid and a protein scaffold. In some embodiments, the ionic liquid is a deep eutectic solvent (DES). In some embodiments, the ionic liquid is antimicrobial. In some embodiments, the ionic liquid includes choline geranate (CAGE). In some embodiments, the ionic liquid is present in an amount of about 0.01% w/w to about 99% w/w, such as 0.01, 0.05, 0.1, 0.5, 1.0, 5, 10, 15, 20, 25, 30, 35, 40, 45, 50, 55, 60, 65, 70, 75, 80, 85, 90, 95, or 99% w/w or greater, or a value within a range defined by any two of the aforementioned values. In some embodiments, the ionic liquid is present in an amount of about 40% w/v.

In some embodiments, the wound care composition includes a scaffold. In some embodiments, the scaffold includes a protein or polysaccharide scaffold including any protein or polysaccharide in solution, for example, collagen, agarose, albumin, alginate, casein, fibrin, fibroin, gelatin, keratin, pectin, elastin, tropoelastin, cellulose, chitosan, chitin, or combinations thereof. In some embodiments, the protein scaffold is electrospun. In some embodiments, the protein scaffold is present in an amount of about 1% w/w to about 99% w/w, such as 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 99% w/w, or greater, or a value within a range defined by any two of the aforementioned values. In some embodiments, the protein scaffold is present in an amount of about 10% w/v.

In some embodiments, the wound care composition includes 40% w/w choline geranate (CAGE) and 10% w/w gelatin.

Some embodiments provided herein relate to a wound dressing. In some embodiments, the wound dressing includes a wound care composition as described herein and a dressing material. In some embodiments, the wound care composition includes an ionic liquid and a protein scaffold. In some embodiments, the wound dressing material is a bandage, a wipe, a sponge, a mesh, a dressing, a gauze, a patch, a pad, tape, or a wrap. In some embodiments, the wound care composition is present in an amount of about 0.005% vol/w % to about 2% vol/w %, such as 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2% volume of wound care composition/weight wound dressing material (vol/w %), or greater, such as 3, 4, 5, 6, 7, 8, 9, 10, 15, 20, 30, 40, or 50% vol/w. In some embodiments, the wound care composition is present in an amount of about 0.625% vol/w %.

In some embodiments is provided a method of making a wound care composition in one of any embodiment described herein. In some embodiments, the method of making a wound care composition includes providing a scaffold solution. In some embodiments, the scaffold solution includes a protein scaffold or polysaccharide scaffold in a solution. In some embodiments, the scaffold is any protein or polysaccharide solution, for example, collagen, agarose, albumin, alginate, casein, fibrin, fibroin, gelatin, keratin, pectin, elastin, tropoelastin, cellulose, chitosan, chitin, or combinations thereof. In some embodiments, the solution is the ionic liquid or an organic solvent. In some embodiments, the organic solvent is a polyamide, a polyacrylonitrile, a polyacetal, a polyester, or a polyketone, or a combination thereof. In some embodiments, the organic solvent is ethanol, ethyl formate, hexafluoro-2-propanol (HFIP), cyclic ethers, acetone, acetates of C2 to C5 alcohol, glyme or dimethoxyethane, methylethyl ketone, dipropyleneglycol methyl ether, lactones, 1,4-dioxane, 1,3-dioxolane, ethylene carbonate, dimethylcarbonate, diethylcarbonate, benzene, toluene, benzyl alcohol, p-xylene, N-methyl-2-pyrrolidone, dimethylformamide, chloroform, 1,2-dichloromethane (DCM), morpholine, dimethylsulfoxide (DMSO), hexafluoroacetone sesquihydrate (HFAS), anisole and mixtures thereof. In some embodiments, the method of making a wound care composition includes providing an ionic liquid. In some embodiments, the ionic liquid is a deep eutectic solvent (DES). In some embodiments, the ionic liquid is choline geranate (CAGE). In some embodiments, the method of making a wound care composition includes mixing the ionic liquid with the protein scaffold solution. In some embodiments, the method of making a wound care composition include electrospinning the mixture of ionic liquid and protein scaffold solution.

In some embodiments, mixing the ionic liquid with the protein scaffold solution is performed at a temperature of about 0, 5, 10, 15, 20, 25, 30, 35, 40, 45, 50, 55, 60, 65, 70, 75, 80, 85, 90, 95, or 100° C. or greater, or a temperature within a range defined by any two of the aforementioned values. In some embodiments, mixing the ionic liquid with the protein scaffold solution is performed at a temperature of about 40° C.

In some embodiments, electrospinning is performed at a temperature of about 0, 5, 10, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, or 100° C. or greater or a temperature within a range defined by any two of the aforementioned values. In some embodiments, electrospinning is performed at a temperature of about 26° C. In some embodiments, electrospinning is performed at a humidity of about 0, 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, or 70% or greater, or a humidity within a range defined by any two of the aforementioned values. In some embodiments, electrospinning is performed at a humidity of about 19%. In some embodiments, electrospinning is performed at a voltage of about 5, 10, 15, 20, 21, 22, 23, 24, 25, 26, 27, 28, 29, 30, 35, 40, 45, or 50V, or greater, or a value within a range defined by any two of the aforementioned values. In some embodiments, electrospinning is performed at a voltage of about 25V. In some embodiments, electrospinning is performed at a flow rate of about 0.01, 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, or 5 mL/hr, or greater or a value within a range defined by any two of the aforementioned values. In some embodiments, electrospinning is performed at a flow rate of about 1 mL/hr.

In some embodiments, the method of making a wound care composition includes desiccating the material to dryness following the electrospinning.

In some embodiments is provided a method of preventing or inhibiting biofilm formation in a subject. In some embodiments, the method of preventing or inhibiting biofilm formation in a subject includes contacting a wound with a wound care composition as described herein. In some embodiments, treatment with a wound care composition prevents biofilm formation. In some embodiments, treatment with a wound care composition reduces bacterial growth and bacterial populations. In some embodiments, treatment with a wound care composition inhibits the growth of S. aureus or P. aeruginosa.

In some embodiments is provided a method of inhibiting, reducing, or preventing the growth of a pathogen. In some embodiments, the method includes contacting a wound with a wound care composition as described herein. In some embodiments, the wound includes a burn, an abrasion, a laceration, a lesion, an ulcer, or a sore. In some embodiments, the wound is infected with a pathogen. In some embodiments, the wound is not infected with a pathogen. In some embodiments, the pathogen is *S. aureus* or *P. aeruginosa*.

In some embodiments is provided a method of enhancing wound healing. In some embodiments, the method includes contacting a wound with a wound care composition as described herein. In some embodiments, the wound comprises a burn, an abrasion, a laceration, a lesion, an ulcer, or a sore. In some embodiments, the wound comprises a diabetic foot ulcer. In some embodiments, enhancing wound healing includes improving, accelerating, or ameliorating wound healing.

Some embodiments provided herein relate to a wound care composition including a scaffold. In some embodiments, the scaffold exhibits anti-proliferative activity towards bacterial or fungal cells, but does not prevent human or mammalian cells from adhering, associating with, or proliferating on the surface.

These features, together with other features herein further explained, are described in greater detail in the following description of the drawings and detailed description.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are, therefore, not to be considered limiting of its scope, the disclosure will be described with additional specificity and detail through use of the accompanying drawings.

DETAILED DESCRIPTION

Figure 1:
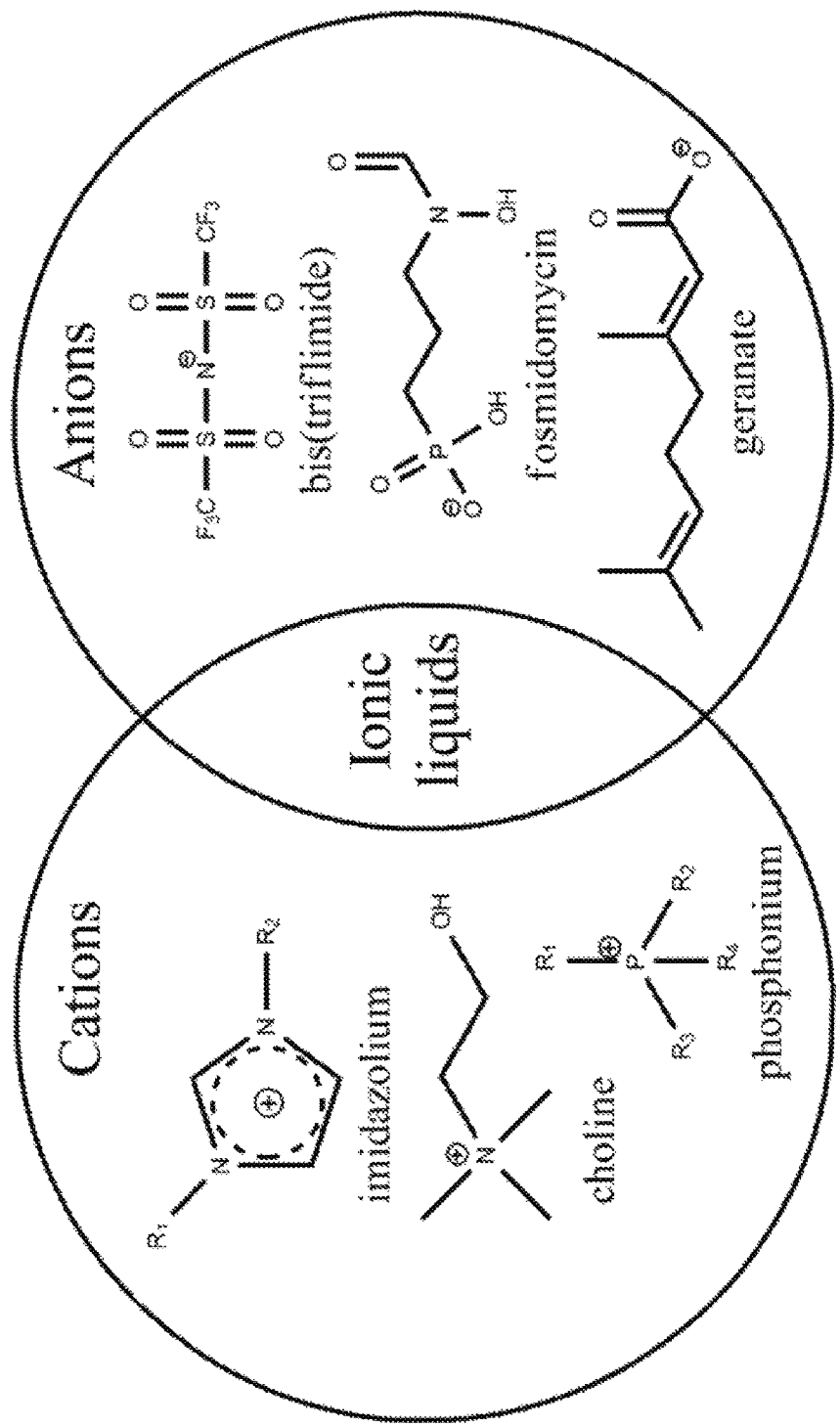
FIG. 1 illustrates the chemical components of one embodiment of ionic liquids (ILs).
Figure 2:
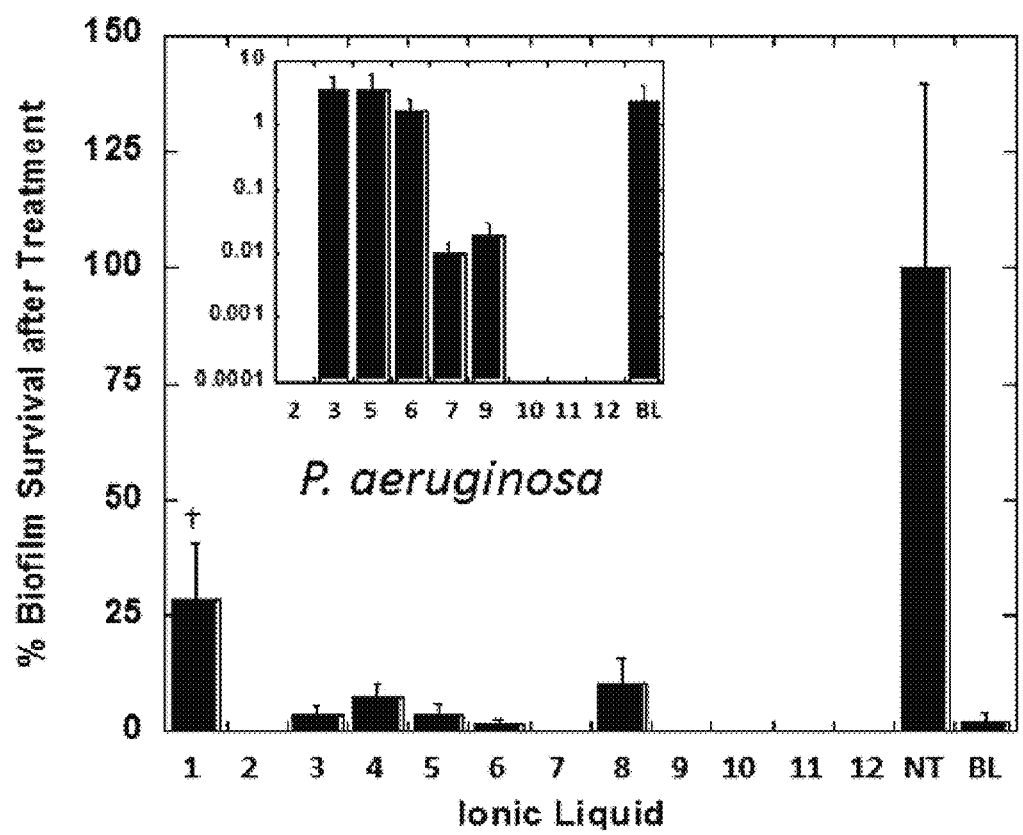
FIG. 2 depicts a graphical representation of the ability of various ionic liquids to kill a biofilm of *P. aeruginosa*. BL=bleach and NT=no treatment. Percent biofilm survival after treatment is shown in the Inset on a log 10 scale to show differences between the most efficacious ILs. Choline geranate (CAGE) is shown as Ionic Liquid 11.
Figure 3:
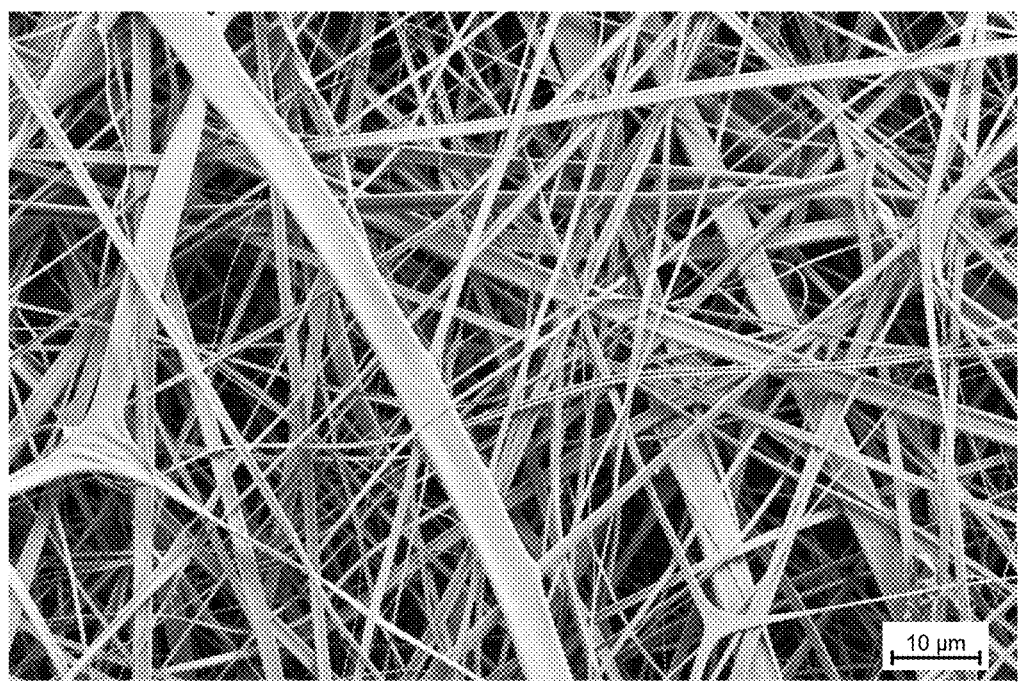
FIG. 3 depicts a scanning electron micrograph of an electrospun gelatin (5% w/v) scaffold, spun at a flow rate of 0.8 mL/hr, with an electric field of 2.91 kV/m.
Figure 4:
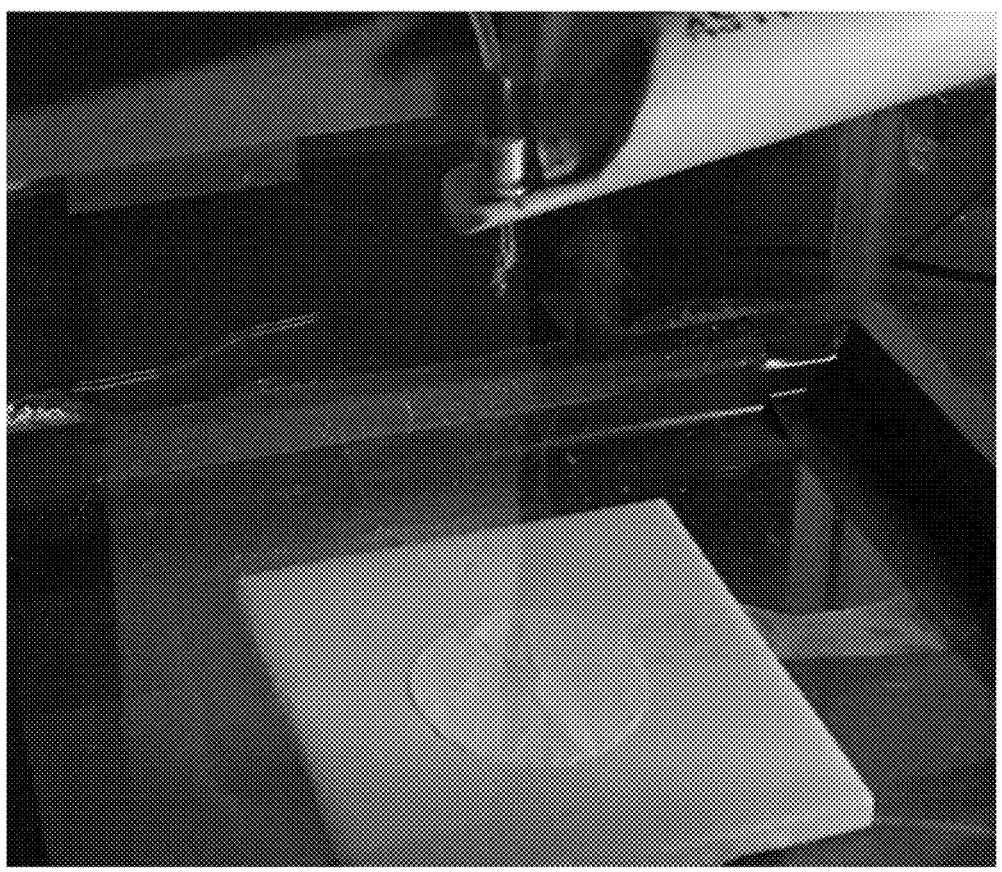
FIG. 4 shows an image of a 0.2% w/v ionic liquid with gelatin scaffold during electrospinning.
Figure 5:
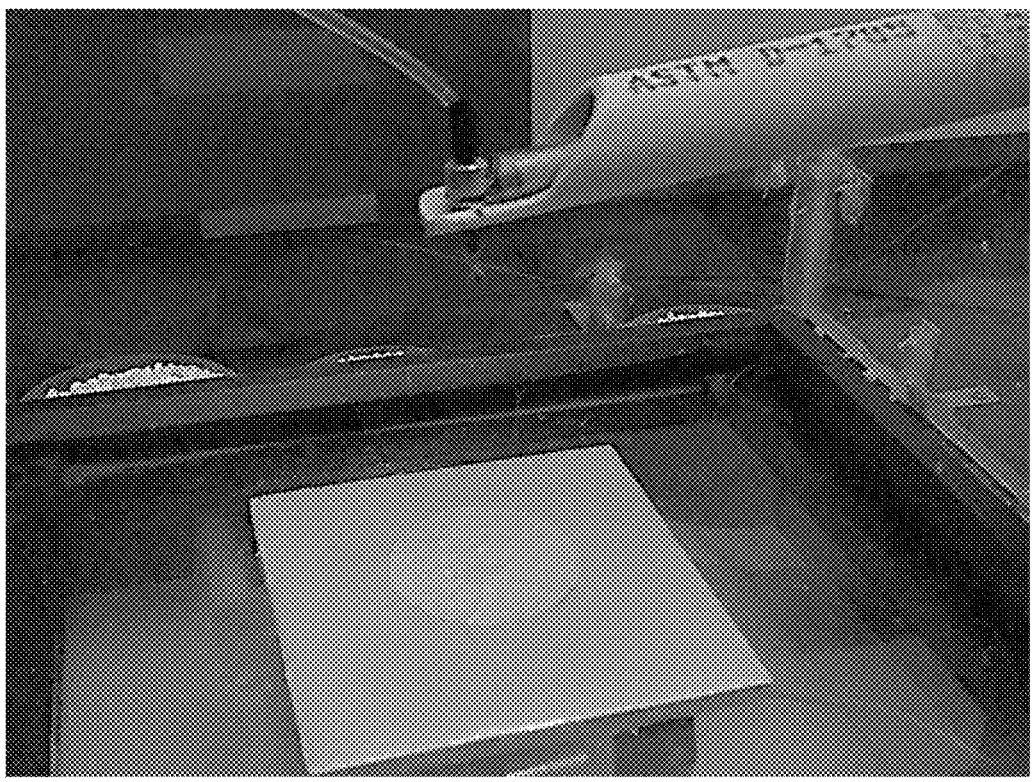
FIG. 5 shows an image of a 1.0% w/v ionic liquid with gelatin scaffold during electrospinning.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the drawings, can be arranged, substituted, combined, separated, and designed in a wide variety of different configurations, all of which are explicitly contemplated herein.

As summarized above, aspects of the wound care compositions and methods making and using the compositions are provided herein.

It is to be understood that this disclosure is not limited to particular embodiments described, as such may, of course, vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

Unless defined otherwise, technical and scientific terms used herein have the same meaning as commonly understood by one of ordinary skill in the art to which the present disclosure belongs. For purposes of the present disclosure, the following terms are defined below.

In some embodiments, provided herein is a method of treating a skin wound. A method of treating a skin wound includes contacting a wound with a wound care composition. In some embodiments, the wound care composition includes an ionic liquid-incorporated scaffold. As used herein, a wound refers to a burn, an abrasion, a laceration, a lesion, an ulcer, or a sore. Wounds include diabetic foot ulcers, severe burns, tumor excision, or trauma. A wound includes damage to the skin, and can include, for example damage caused by trauma, burn, surgery, or other type of damage. In some embodiments, the method of treating a skin wound enhances wound healing, prevents pathogen biofilm formation, inhibits pathogen growth and proliferation, inhibits sepsis, and prophylactically prevents the formation of biofilm or growth of pathogens. In some embodiments, the wound is skin damage, a burn, an abrasion, a laceration, an incision, a sore, a puncture wound, a penetration wound, a gunshot wound, or a crushing injury.

In some embodiments, the wound healing composition is applied to the wound at least once daily. In some embodiments, the wound healing formulation is applied to the wound three times a day. In some embodiments, applying the wound healing formulation provides a wound healing rate that is accelerated in comparison to a healing rate of a non-treated wound. In some embodiments, the formulation is applied in an amount effective to accelerate wound healing, promote wound closure, or cause wound regression. In some embodiments, the applying the formulation reduces, attenuates, or prevents bacterial growth or infection in the wound. In some embodiments, the composition does not prevent human or mammalian cells from proliferating.

In some embodiments is provided a wound care composition that includes an ionic liquid and a protein scaffold. In some embodiments, the composition may be used alone, for example, for direct application to a wound. Thus, for example, the composition may be formulated as an ointment, a cream, a spray, a spritz, a mist, a liquid, a gel, a lotion, or a solution. In some embodiments, the composition may be topically applied to a wound. In some embodiments, the composition may be administered subcutaneously.

In some embodiments, the composition may be configured for incorporation into a wound dressing material, including a bandage, a wipe, a sponge, a mesh, a dressing, a gauze, a patch, a pad, tape, or a wrap, or other wound dressing material. The composition may be used to saturate, impregnate, cover, coat, or otherwise be incorporated into a wound dressing material.

As referred to herein, the term "ionic liquid" (IL) refers a family of molecules commonly composed of an organic alkyl cation paired with either an organic or inorganic anion. These materials all have a melting point below 100° C., and are frequently described as "molten salts". The chemical nature of the cation and anion components of an IL are readily modified, and as such, the physiochemical properties of the salt as a whole can be "tuned" for optimal use within a variety of applications (Hassan et al., Studies on the dissolution of glucose in ionic liquids and extraction using the antisolvent method. *Environmental science & technology* 47(6):2809-2816, 2013; Frederix M, et al., Development of a native *Escherichia coli* induction system for ionic liquid tolerance. *PloS one* 9(7):e101115, 2014; Eisenberg, Ionic interactions in biological and physical systems: a variational treatment. *Faraday discussions* 160:279-296, 2013; Cao Y, et al., Separation of soybean isoflavone aglycone homologues by ionic liquid-based extraction. *Journal of agricultural and food chemistry* 60(13):3432-3440, 2012; De Diego et al., A recyclable enzymatic biodiesel production process in ionic liquids. *Bioresource technology* 102(10):6336-6339, 2012); each of which is incorporated by reference herein in its entirety). As used herein, "deep Eutectic Solvents" (DESs) are broadly defined as a mixture of charged and neutral species, either in equimolar or imbalanced ratios, that, when combined, have a much lower melting point than the individual component. DESs are mixtures of compounds and neutral molecules and ILs are themselves ionic compounds. The ionic liquid described herein, including DESs are intimately related on a chemical level and both are considered part of a larger class of molecules.

A number of ILs have shown a propensity to disrupt the noncovalent bonds within the structure of recalcitrant biopolymers such as cellulose or keratin (Lovejoy, et al. (2011) Tetraalkylphosphonium-Based Ionic Liquids for a Single-Step Dye Extraction/MALDI MS Analysis Platform. *Anal Chem* 83(8):2921-2930; Lovejoy et al. (2012) Single-Pot Extraction-Analysis of Dyed Wool Fibers with Ionic Liquids. *Anal Chem* 84(21):9169-9175; Shill K, et al. (2011) Ionic liquid pretreatment of cellulosic biomass: enzymatic hydrolysis and ionic liquid recycle. *Biotechnology and bioengineering* 108(3):511-520; each of which is incorporated by reference herein in its entirety).

This aspect of IL chemistry has played an important role in the processing, disruption and dissolution of biopolymers for applications in renewable energy and forensics (Zhang J, et al. (2014) Understanding changes in cellulose crystalline structure of lignocellulosic biomass during ionic liquid pretreatment by XRD. *Bioresource technology* 151:402-405; Uju, et al. (2013) Peracetic acid-ionic liquid pretreatment to enhance enzymatic saccharification of lignocellulosic biomass. *Bioresource technology* 138:87-94; Varanasi P, et al. (2013) Survey of renewable chemicals produced from lignocellulosic biomass during ionic liquid pretreatment. *Biotechnology for biofuels* 6(1):14; Lovejoy, et al. (2011) Tetraalkylphosphonium-Based Ionic Liquids for a Single-Step Dye Extraction/MALDI MS Analysis Platform. *Anal Chem* 83(8):2921-2930; Lovejoy et al. (2012) Single-Pot Extraction-Analysis of Dyed Wool Fibers with Ionic Liquids. *Anal Chem* 84(21):9169-9175; each of which is incorporated by reference herein in its entirety).

The ability of ILs to disrupt biopolymers has also enabled their use as novel antibiotic agents that specifically target bacterial biofilms and have a bactericidal effect in general. Biofilms are communities of microbes that secrete a thick layer of exopolymeric material (including polysaccharides, proteins and nucleic acids) that effectively serve as a physical barrier to treatment with antibiotics (Donlan et al. (2001) Biofilms and device-associated infections. *Emerg Infect Dis* 7(2):277-281; Flemming et al. (2010) The biofilm matrix. *Nature Reviews Microbiology* 8(9):623-633; each of which is incorporated by reference herein in its entirety). Typical applications of prescribed antibiotics do not efficiently pass through this physical barrier, and thus, biofilm bacteria are often 500-1000 times less susceptible to antibiotic treatment than their planktonic counterparts. Bacterial biofilms are responsible for most hospital-acquired infections, and the CDC has estimated the cost of combatting these maladies alone exceeds $10 billion per year (Bickers et al. (2006) The burden of skin diseases: 2004—A joint project of the American Academy of Dermatology Association and the Society for Investigative Dermatology. *J Am Acad Dermatol* 55(3): 490-500). Antibacterial ILs disrupt the biofilm's protective exopolymeric layer and re-enable efficient antibiotic delivery to the cells within it, and sometimes have antibacterial properties themselves (Zakrewsky et al. (2014) Ionic liquids as a class of materials for transdermal delivery and pathogen neutralization. *P Natl Acad Sci USA* 111(37):13313-13318; Lovejoy et al. (2012) Utilization of Metal Halide Species Ambiguity to Develop Amorphous, Stabilized Pharmaceutical Agents As Ionic Liquids. *Cryst Growth Des* 12(11): 5357-5364; each of which is incorporated by refereince herein in its entirety).

As used herein, the term "choline geranate" refers to a specific DES that combines choline with geranate anion and geranic acid. This formulation of choline geranate is referred to herein as CAGE. CAGE shows potent antibiofilm properties against pathogens associated with common skin infections (including, for example, *Staphylococcus aureus, Pseudomonas aeruginosa*), including multi-drug resistant isolates (e.g. Methicillin resistant *S. aureus*, or MRSA). CAGE exhibits low toxicity toward human epithelial cells and C3H/HeJ mice systematically exposed to CAGE (50 μL/day, for seven days, n=4) do not show any local or systemic inflammation following exposure. Further, CAGE not only neutralizes biofilms in vitro, but is also capable of passing through the dermis to address infections that lie below the outer layers of the skin. This aspect of the compound has significant ramifications for its use as an antibiofilm agent to treat established skin infections (such as necrotizing infections, chronic wounds, or diabetic ulcers) but also as a prophylactic to insure that infections do not establish in surgical wounds during the process of wound healing. CAGE is particularly effective both at neutralizing bacterial biofilms in vitro and traversing dermal layers to treat biofilms that exist within skin (Zakrewsky et al. (2014) Ionic liquids as a class of materials for transdermal delivery and pathogen neutralization. *P Natl Acad Sci* USA 111(37): 13313-13318). The development of ionic liquid-modified wound healing scaffolds will render the scaffolds themselves resistant to contamination with biofilms and enhance healing in difficult to treat patients. ILs are capable of preventing biofilm formation on wound healing devices without changing the structure and efficacy of the device.

In some embodiments, composition including an IL is added, incorporated, coated on, applied to, saturated with, impregnated with, covered with, or otherwise be incorporated or contacted with a wound dressing material in an amount of 0.005% to 2% volume IL to weight gauze (vol/w %), such as 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2% volume of wound care composition/weight wound dressing material (vol/w %), or greater, such as 3, 4, 5, 6, 7, 8, 9, 10, 15, 20, 30, 40, or 50% vol/w or an amount within a range defined by any two of the aforementioned values. In some embodiments, the wound care composition is present in an amount of about 0.625% vol/w %. In some embodiments, the IL is contacted with a wound dressing in an amount of 0.05 μg per mg wound dressing material to 20 μper mg wound dressing material, such as 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20 μg/mg, or an amount within a range defined by any two of the aforementioned values. In some embodiments, the wound care composition is present in an amount of about 6.25 μg/mg. Thus, in some embodiments, the composition including an IL is incorporated into a wound dressing material, for example, to saturate, impregnate, cover, coat, or otherwise be incorporated into the wound dressing material. Coating can include, for example, dip coating or surface modifying a material with an IL.

In some embodiments, the amount of IL incorporated into an electrospun scaffold can be 0.01% w/w to about 99% w/w, such as 0.01, 0.05, 0.1, 0.5, 1.0, 5, 10, 15, 20, 25, 30, 35, 40, 45, 50, 55, 60, 65, 70, 75, 80, 85, 90, 95, or 99% w/w or greater, or a value within a range defined by any two of the aforementioned values. In some embodiments, the IL is present in an amount of about 40% w/v.

As used herein, pathogens can include opportunistic pathogens associated with skin infections, including, for example, bacterial infections (including, for example, *Staphylococcus aureus, Pseudomonas aeruginosa*, methicillin resistant *S. aureus* (MRSA), *Streptococcus pyogenes*), viral infections, fungal infections, or yeast infections. In some embodiments, the compositions provided herein prevent pathogenic growth. In some embodiments, the compositions do not prevent human or mammalian cell proliferation. In some embodiments, the compositions do not prevent human or mammalian cells from adhering, associating with, or proliferating on a scaffold or surface.

As used herein a scaffold refers to a material that acts as a foundation or structure for the formulation of the wound care compositions as described herein. The scaffold may be a protein scaffold or a polysaccharide scaffold and may include a molecule for structural formation, including, for example any protein solution, including, for example, one or more of collagen, agarose, albumin, alginate, casein, elastin, fibrin, fibroin, fibronectin, gelatin, keratin, laminin, pectin, elastin, tropoelastin, cellulose, chitosan, chitin. In some embodiments, the wound care composition is prepared by electrospinning a protein scaffold incorporated with IL. In some embodiments, the amount of protein scaffold, can be 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19% or 20% w/v or greater, or a value within a range defined by any two of the aforementioned values.

The protein scaffold can be in solution, for example, in a solvent. In some embodiments, the solvent is the IL. In some embodiments, the solvent is an organic solvent. In some embodiments, the organic solvent is a polyamide, a polyacrylonitrile, a polyacetal, a polyester, or a polyketone, or a combination thereof. In some embodiments, the organic solvent is ethanol, ethyl formate, hexafluoro-2-propanol (HFIP), cyclic ethers (tetrahydrofuran (THF), and 2,5-dimethylfuran (DMF)), acetone, acetates of C2 to C5 alcohol (such as ethyl acetate and butyl acetate), glyme or dimethoxyethane (monoglyme, ethyl glyme, diglyme, ethyl diglyme, triglyme, butyl diglyme, tetraglyme, dimethyl glycol, ethylene glycol dimethyl ether, dimethyl cellosolve, and DME), methylethyl ketone (butanone), dipropyleneglycol methyl ether, lactones (such as δ-valerolactone, γ-valerolactone, b-butyrolactone, g-butyrolactone), 1,4-dioxane, 1,3-dioxolane, ethylene carbonate, dimethylcarbonate, diethylcarbonate, benzene, toluene, benzyl alcohol, p-xylene, N-methyl-2-pyrrolidone, dimethylformamide, chloroform (trichloromethane, methyl trichloride), 1,2-dichloromethane (DCM), morpholine, dimethylsulfoxide (DMSO), hexafluoroacetone sesquihydrate (HFAS), anisole (methoxybenzene) and mixtures thereof.

Electrospun materials have been described since 1934 (Garg et al. Electrospinning jets and nanofibrous structures." *Biomicrofluidics* 5.1: 013403, 2011). Since then a plethora of proteins and polymers have been electrospun into scaffolds for use in clinical and research realms. The principle behind electrospinning is to eject a solubilized protein through a charged nozzle onto an oppositely charged target. When the surface tension forces are balanced with the electric field, the protein droplet elongates forming a funnel shape known as a Taylor cone (Taylor. Electrically driven jets. *Proceedings of the Royal Society of London A: Mathematical, Physical and Engineering Sciences*. Vol. 313. No. 1515. The Royal Society, 1969). However, the stability of the cone was a problem until 1987 when Hayati discovered that semiconducting insulating liquids created more stability at higher voltages (Hayati et al., Investigations into the mechanisms of electrohydrodynamic spraying of liquids: I. Effect of electric field and the environment on pendant drops and factors affecting the formation of stable jets and atomization. *Journal of Colloid and Interface Science* 117.1: 205-221, 1987). The stable cone and ejection of the solubilized protein causes the solvent to evaporate before the target is reached and the creation of nanofibers being laid upon the target in a nonwoven pattern.

In 1971, Baumgarten determined that by varying the concentration of protein and changing the applied voltage, the diameter of the nanofibers could be manipulated, with a higher concentration producing larger continuous fibers and lesser concentrations producing shorter and finer fibers (Baumgarten, Electrostatic spinning of acrylic microfibers. *Journal of colloid and interface science* 36.1: 71-79, 1971).

Provided herein are electrospinning methods for the creation of novel protein scaffolds that serve as wound healing agents. These scaffolds are fabricated using native skin proteins and as a result, they more closely match the composition and architecture of skin, thereby enhancing wound healing.

The novelty of the embodiments and alternatives described herein includes the combination of ILs and protein scaffolds to enhance the wound healing process. The development of IL-modified wound healing scaffolds mitigates biofilm formation on these scaffolds and enhances healing in difficult to treat patients.

As used herein, the term "treatment" refers to an intervention made in response to a wound, such as a burn or other wound, including difficult to treat wounds, in a subject in need. The aim of treatment may include, but is not limited to, one or more of the alleviation or prevention of symptoms, slowing or stopping the progression or worsening of a wound, enhancement of the wound healing, and the remission of the wound. In some embodiments, "treatment" refers to both therapeutic treatment and prophylactic or preventative measures. Those in need of treatment include those already affected by a wound as well as those in which an infection of the wound is to be prevented.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy.

Treatment may include administration of a wound care composition alone or a wound dressing material that has a wound care composition incorporated therein. When used alone, the wound care composition may be administered topically, orally, subcutaneously, or in other means in order to properly treat the wound. When the wound care composition is incorporated into a wound dressing material, the wound dressing material is applied to the wound to treat the wound.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. A subject in need includes a subject that is suffering from a wound, including a burn (including a severe, moderate, or minor burn), trauma, surgical wound, a laceration, a lesion, an ulcer, or a sore. In some embodiments, the subject suffers from a diabetic foot ulcer.

As used herein, the term "prevention" refers to any activity that reduces the burden of the individual later expressing wound symptoms. This can take place at primary, secondary, and/or tertiary prevention levels, wherein: a) primary prevention avoids the development of symptoms/condition; b) secondary prevention activities are aimed at early stages of the condition/symptom treatment, thereby increasing opportunities for interventions to prevent progression of the condition/symptom and emergence of symptoms; and c) tertiary prevention reduces the negative impact of an already established condition/symptom by, for example, restoring function and/or reducing any condition/symptom or related complications.

The articles "a" and "an" are used herein to refer to one or to more than one (to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In certain embodiments, the "purity" of any given agent in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

Example 1

Choline Geranate Synthesis and Preparation

The following example demonstrates one embodiment of a method of synthesizing CAGE for use in an IL-incorporated wound dressing.

CAGE was synthesized from commercially available reagents using equipment standard to the organic chemistry laboratory. Geranic acid typically requires purification via recrystallization from acetone. The product was characterized with standard methods (including, for example, NMR, UV, or IR) to verify purity. CAGE was synthesized through salt metathesis of 1:2 molar ratio choline bicarbonate and geranic acid, and the final product possessed both fluidity and transparency at room temperature. Two equivalents of neat geranic acid (50.0 g, 0.297 moles, Sigma-Aldrich, St. Louis, Mo.), were recrystallized five times at −70° C. in acetone, in a 500-mL round bottom flask and added to one equivalent of choline bicarbonate (80 wt % solution, 30.7 g, 0.149 moles, Sigma-Aldrich, St. Louis, Mo.). The mixture was stirred at room temperature until $CO_2$ evolution ceased. Residual $H_2O$ was removed by rotary evaporation at 60° C. for 2 h and drying in a vacuum oven for 24 h at 60° C.

Physical characterization at 25° C. was in good agreement with published values and was as follows: density, 0.989±0.001 g mL$^{-1}$; and conductivity, 0.0427±0.0005 mS cm$^{-1}$.

Physicochemical properties were identical to those previously published confirming purity (Zakrewsky et al., PNAS, 2014, 111, 13313; incorporated by reference herein in its entirety). CAGE has unique properties based upon the 1:1:1 ratio of cation:anion:protonated acid. This is important since it gives rise to the low conductivity determined for CAGE (0.043 mS cm$^{-1}$) and is a potential indicator of anti-biofilm efficacy but, also provides insight to minimized skin irritation potential.

Composition was confirmed with nuclear magnetic resonance spectroscopy (NMR). NMR assignments were also in good agreement with published assignments and were as follows: 1 H NMR (DMSO-d$_6$), δ 5.57 (s, 2H), 5.07 (t, J=6.1, 2H), 3.85 (t, J=6.6, 2H), 3.42 (t, J=6.6, 2H), 3.17 (s, 9H), 2.60 (m, 4H), 2.00 (m, 4H), 1.93 (s, 6H), 1.70 (s, 2H), 1.64 (s, 6H), and 1.57 (s, 6H); $^{13}$C NMR (DMSO-d$_6$), δ 170.3, 150.4, 131.5, 124.0, 121.7, 67.6, 55.6, 53.5, 40.4, 32.8, 25.8, and 17.8.

CAGE may be incorporated into a wound care composition, such as a dressing or bandage. For example, CAGE may be deposited onto the surface of medical-grade gauze using standard dip-coating protocols. Application of the IL at various concentrations (μmol per cm$^2$) is established by dissolving the IL into an appropriate solvent (e.g. acetone) at various concentrations after which the dressings are coated and allowed to dry. Exemplary IL concentrations include 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or 2% volume of wound care composition/weight wound dressing material (vol/w %), or greater, such as 3, 4, 5, 6, 7, 8, 9, 10, 15, 20, 30, 40, or 50% vol/w, or an amount within a range defined by any two of the aforementioned values. In some embodiments, the wound care composition is present in an amount of about 0.625% vol/w %. In some embodiments, the amount of IL incorporated into an electrospun scaffold can be 0.01% w/w to about 99% w/w, such as 0.01, 0.05, 0.1, 0.5, 1.0, 5, 10, 15, 20, 25, 30, 35, 40, 45, 50, 55, 60, 65, 70, 75, 80, 85, or 90, 95, or 99% w/w or greater, or a value within a range defined by any two of the aforementioned values. In some embodiments, the IL is present in an amount of about 40% w/v.

Extraction of a defined weight of the gauze, followed by gravimetric and/or HPLC analysis (with a geranic acid standard) may be used to verify deposition of the appropriate amounts of IL within this procedure. CAGE is unreactive toward the cotton fibers in gauze, but effects (if any) of the deposition on various material may be determined by analysis of treated and un-treated samples with SEM.

Example 2

Electrospinning of IL-Incorporated Wound Dressings

The following example demonstrates one embodiment of a method for electrospinning IL-incorporated wound dressings.

Ionic liquids are incorporated into a protein solution and electrospun onto targets to create novel wound dressings that include CAGE, thereby forming IL wound dressings. The resulting scaffolds are evaluated using SEM for porosity and fiber diameter and compared to known control scaffolds to understand how the inclusion of CAGE affects the architecture of the scaffold. Additionally, mechanical strength testing and characterization are also performed on the IL wound dressing. Last, using HPLC techniques, the inclusion of IL into the wound dressing is confirmed.

Electrospinning was performed under various conditions, as set forth in Table 1. All samples were performed at 26° C., 18% humidity, and at a flow rate of 1 mL/hr. The distance refers to the distance from the electrospin needle to the target. The % IL refers to the final percentage in the product.

TABLE 1

| Electrospinning Conditions | | | |
|---|---|---|---|
| % Ionic Liquid (w/w) | % Gelatin (w/v) | Voltage (V) | Distance (cm) |
| 1 | 0 | 10 | 30 | 12 |
| 2 | 0.2 | 10 | 25 | 9 |
| 3 | 0.7 | 10 | 25 | 9 |
| 4 | 1.0 | 10 | 25 | 9 |

Figure 6A:
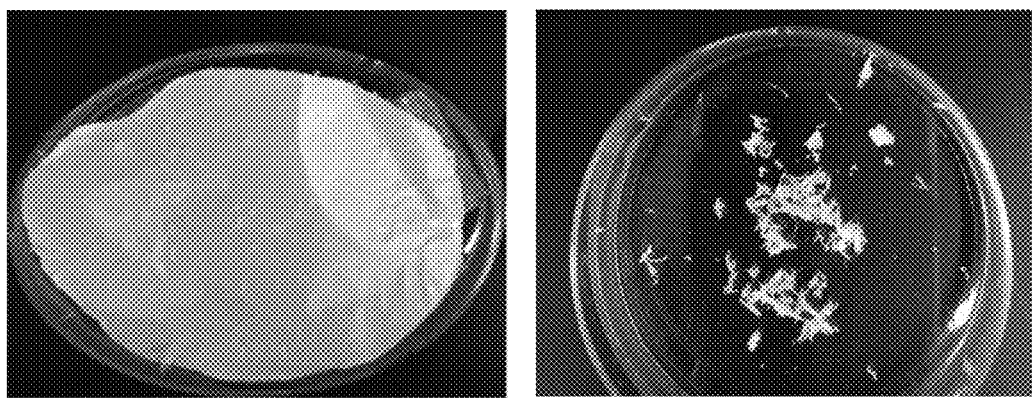
FIG. 6A shows an image of an electrospun product having 10% w/v gelatin scaffold in hexafluoro-2-propanol (HFIP), spun at 30V, at a flow rate of 1 mL/hr, with a distance of the needle to target of 12 cm, at 26° C. in 18% humidity.
Figure 6B:
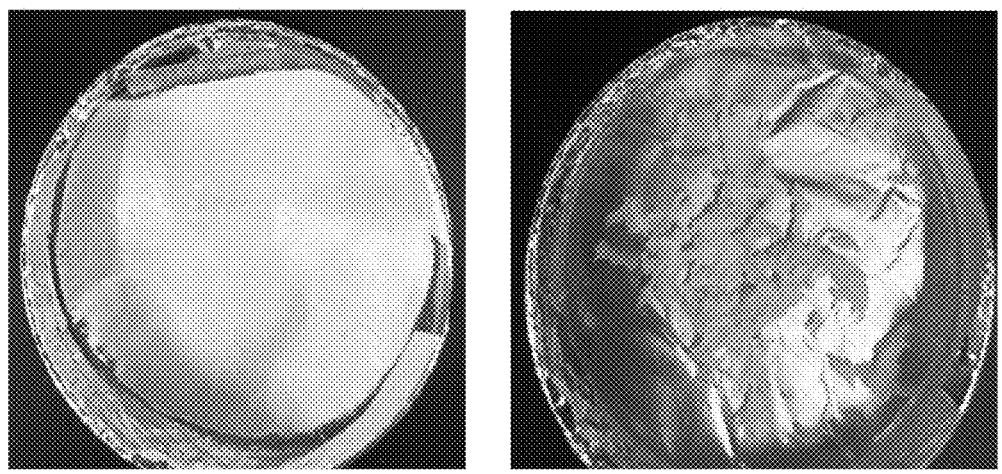
FIG. 6B shows an image of an electrospun product having 10% w/v gelatin scaffold in HFIP plus 0.2% ionic liquid, spun at 25V, at a flow rate of 1 mL/hr, with a distance of the needle to target of 9 cm, at 26° C. in 18% humidity.

FIGS. 6A-6B show the product that result from each of the conditions shown in Table 1.

The purpose of this experiment was to manipulate the concentration of IL, CAGE, within a 5 mL, 10% gelatin in hexafluoro-2-propanol (HFIP) solution to effectively incorporate the IL into a final electrospun gelatin scaffold, in the effort of providing the scaffold with an antimicrobial aspect. HFIP is toxic and corrosive.

The method of electrospinning was carried out with a 0.02% w/w concentration of IL in liquid mixture (0.2% w/w concentration of IL in product). 0.5001 g of solid gelatin was weighed out and placed into a glass bottle along with a magnetic stir bar. Next, 5 mL of HFIP was added to the bottle with the gelatin. The bottle was then covered completely with aluminum foil to inhibit the IL from reacting with the light upon being added to the solution. 1 μL of IL was then added to the bottle using a 1 μL-10 μL pipette; the tip was removed after the IL was dispensed, and a 5 mL syringe was used to push air through the tip in an effort to release any liquid IL remaining in the tip. The bottle was capped and placed in a water bath on top of a stir/heat plate. The temperature of the bath was monitored to ensure it did not exceed 40° C. (human body temperature). The solution was stirred for approximately 30 minutes, where the heat was set to "low" while the stir speed was set to about 4. The entire bath was covered with foil and the laboratory lights were shut off during this period (to avoid light exposure of the IL). Once the solution was mixed, until it was a homogeneous mixture, it was placed in the fridge overnight. The gelatin solution was stirred again for about twenty minutes prior to electrospinning.

The solution containing 0.02% w/w IL (liquid form) was electrospun following the general protocol for electrospinning, while the parameters were as follows: temperature, 26° C.; humidity, 19%; distance from needle to target, 9 cm; voltage, 25V; flow rate, 1 mL/hr.

Once the process commenced, the aluminum target was not immediately covered with visible white solid product (FIG. 6B) in comparison to a control gelatin solution without the incorporated IL (FIG. 6A). However, once the scaffold's texture appeared to be uneven with drops, concentrated product spread throughout the scaffold. Because ILs are extremely conductive, the "crackling" sound of the electricity throughout the system was increased, in comparison to electrospinning a control.

Once an hour had passed while electrospinning, the gelatin scaffold with 0.2% IL was placed in a desiccator for twenty-four hours to ensure that the scaffold completely dried.

Data/Calculations (0.2% Ionic Liquid in Final Product)
Mass of gelatin: 0.5001 g
Volume of HFIP: 5 mL
Volume of ionic liquid: 1 μL (0.2% in product)
Percent weight/volume (for mass of gelatin and volume of HFIP)
10%=10 g/100 mL
0.5 g gelatin/5 mL HFIP For volume/concentration of ionic liquid: 5 mL (total volume)×0.2% (desired concentration of ionic liquid in product)=1.0 μL ionic liquid.

FIG. 6B shows the 0.2% ionic liquid-concentrated gelatin scaffold being electrospun.

The same procedure used for the 10% gelatin scaffold in 5 mL HFIP with 0.2% incorporated IL may be used to create additional mixtures with IL, for example, with concentrations of 0.7% and 1.0% IL in the final gelatin scaffolds. The parameters for electrospinning were kept the same for these additional mixtures. A control scaffold was also spun, with the same amount of gelatin in HFIP. The distance from the needle to the target was returned to 12 cm for the control.

Data/Calculations (0.7% Ionic Liquid in Final Product)
Mass of gelatin: 0.5006 g
Volume of HFIP: 5 mL
Volume of ionic liquid: 3.5 μL
Percent weight/volume
10%=10 g/100 mL
0.5 g gelatin/5 mL HFIP For volume/concentration of ionic liquid: 5 mL (total volume×0.7% (desired concentration of ionic liquid in product)=3.5 μL ionic liquid.

Figure 6C:
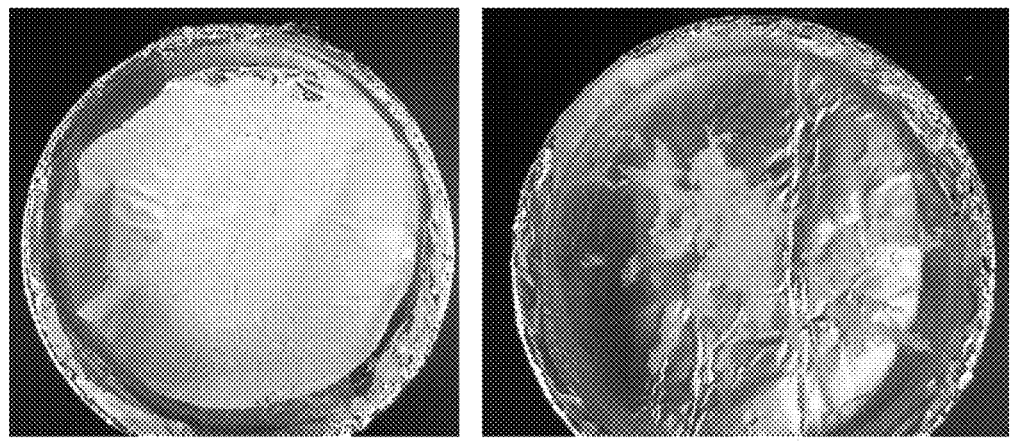
FIG. 6C shows an image of an electrospun product having 10% w/v gelatin scaffold in HFIP plus 0.7% ionic liquid, spun at 25V, at a flow rate of 1 mL/hr, with a distance of the needle to target of 9 cm, at 26° C. in 18% humidity.

Similar to the first IL-concentrated solution that was spun, the aluminum target turned white after a longer period than normal. The sound of the electricity again was more prominent than with a control, but not much different from the first IL-spun scaffold. The texture of the final product was not as smooth as a control scaffold, with more droplet-structures upon the surface, as shown in FIG. 6C.

Data/Calculations (1.0% Ionic Liquid in Final Product)
Mass of gelatin: 0.5001 g
Volume of HFIP: 5 mL
Volume of ionic liquid: 5.0 μL
Percent weight/volume
10%=10 g/100 mL
0.5 g gelatin/5 mL HFIP For volume/concentration of ionic liquid: 5 mL (total volume)×1.0% (desired concentration of IL in product)=5.0 μL ionic liquid.

Figure 6D:
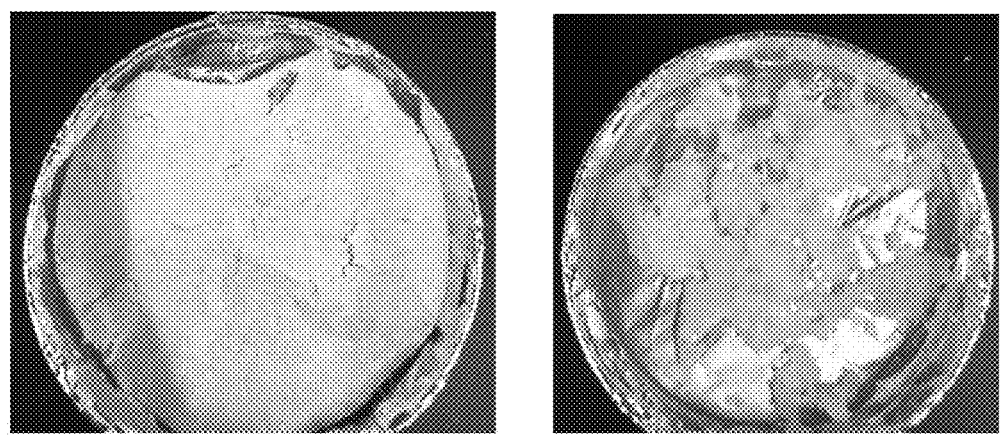
FIG. 6D shows an image of an electrospun product having 10% w/v gelatin scaffold in HFIP plus 1.0% ionic liquid, spun at 25V, at a flow rate of 1 mL/hr, with a distance of the needle to target of 9 cm, at 26° C. in 18% humidity. Each of FIGS. 6A-6D show the scaffold before being removed from the foil (left) and after removal from foil (right).

The observation of the loud sound of electricity noted from the two previous scaffolds was again present. However, the target began to turn white quicker, and again, the texture of the final product consisted of droplets instead of being smooth, as shown in FIG. 6D.

Upon removing the scaffolds from the desiccator eight days later, the scaffolds were difficult to remove from the aluminum targets, and therefore came off in broken-up pieces.

NMR Data

Figure 7:
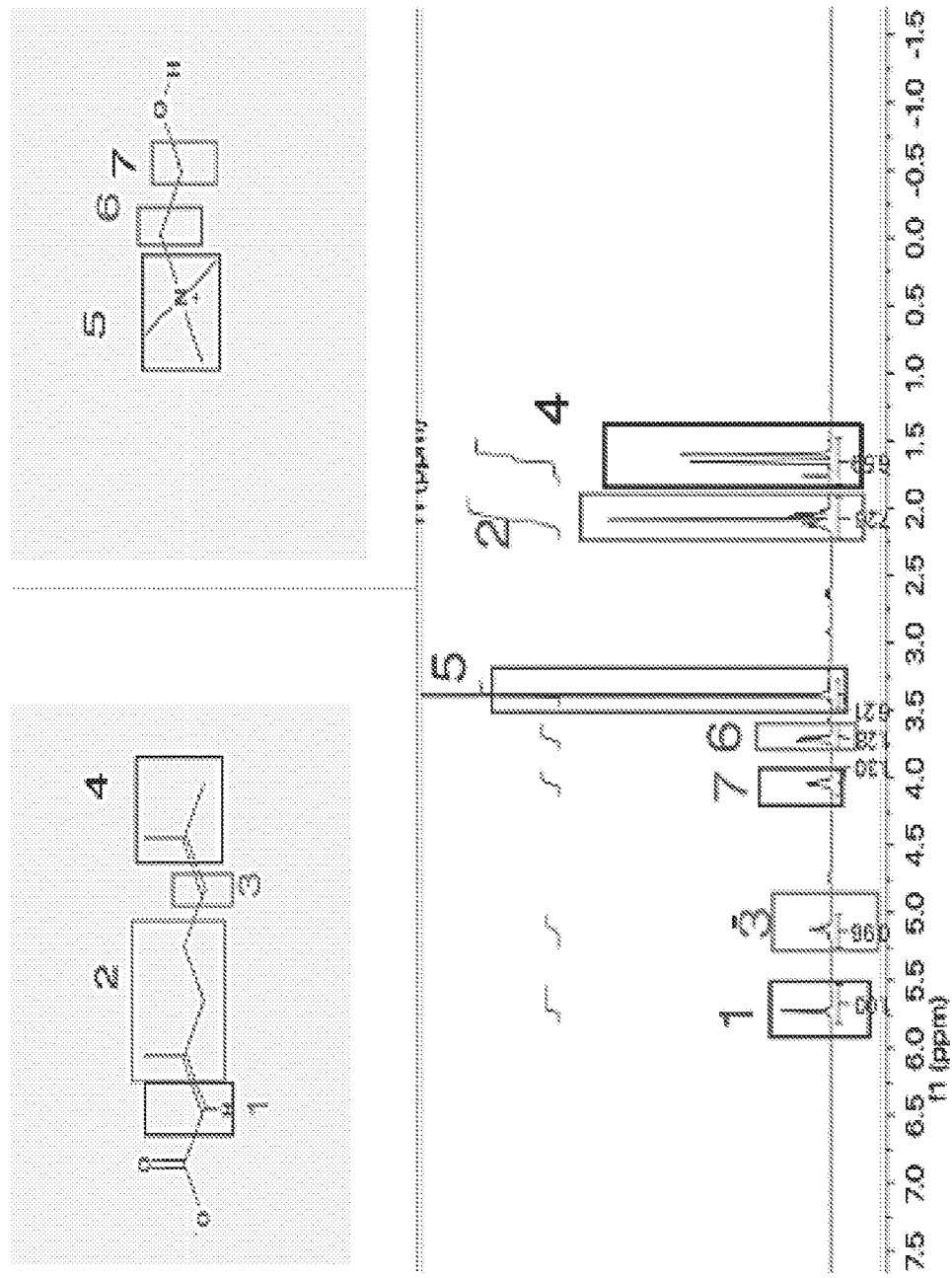
FIG. 7 depicts structures of geranate (top left) and choline (top right), with an NMR spectrum of choline geranate (CAGE).

FIG. 7 shows the molecular structure of geranate (top left) and choline (top right). The bottom photo is the NMR spectrum showing the presence of the two ions in the gelatin scaffold.

To verify inclusion of CAGE within the IL-incorporated scaffolds, a small portion (~1 mg) of the dried scaffold material was placed into a test tube along with 0.7 mL of deuterated acetone (acetone-d6, 99.9%, Sigma-Aldrich) and the mixture was incubated overnight at room temperature with periodic mixing. A similar extraction was performed on a control scaffold that was not incorporated with IL. The extracted acetone was removed from the extraction vessel and placed into an NMR tube, and analyzed via $^1$NMR (400 MHz, Bruker). The biological activity of the extracted IL is also assessed using the broth microdilution assay against *Staphylococcus aureus* and *Pseudomonas aeruginosa*.

Figure 8:
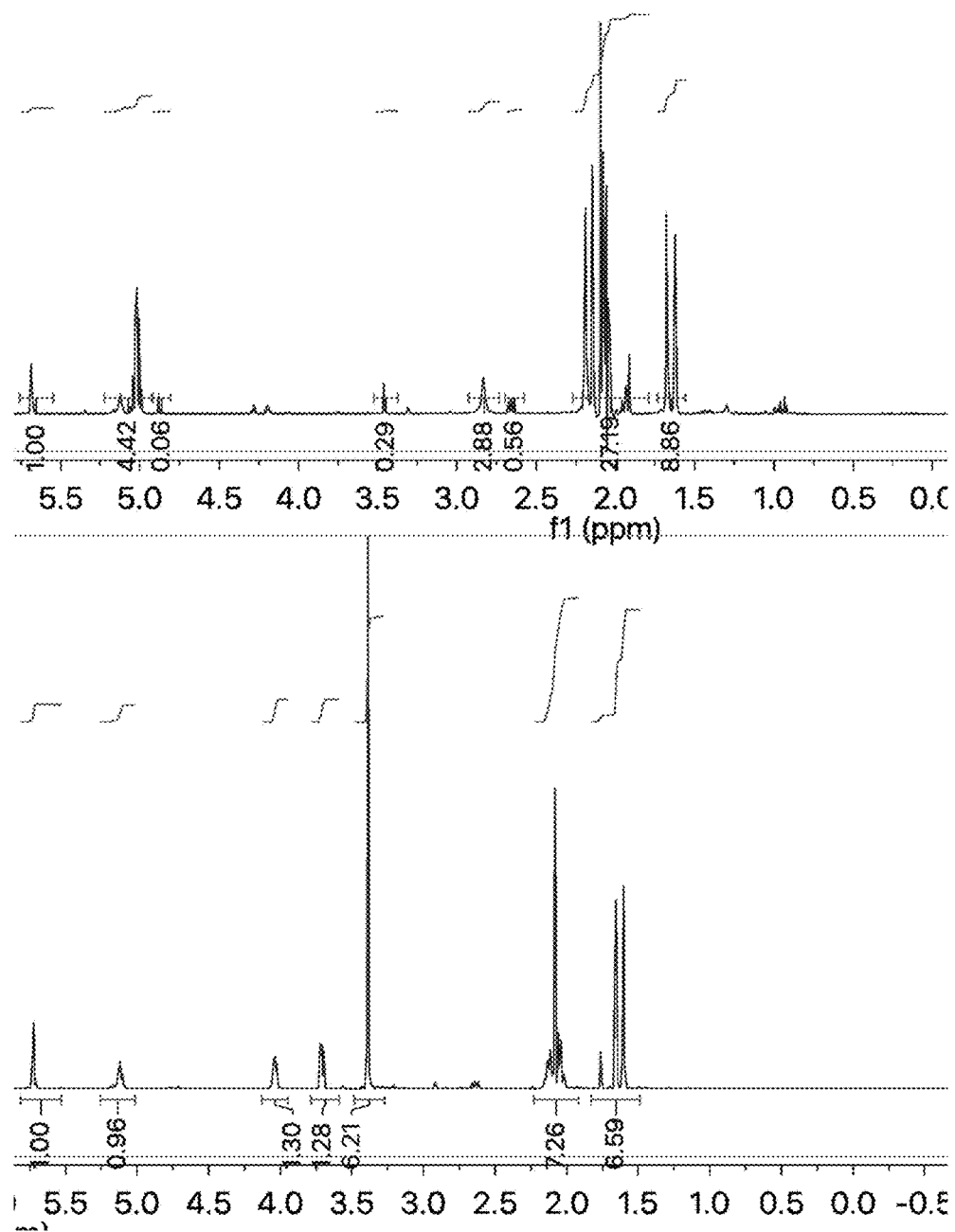
FIG. 8 depicts NMR spectra of the ionic liquid-incorporated scaffolds, indicating the presence of choline geranate incorporated scaffold (top), compared to choline geranate (CAGE) alone (bottom).
Figure 9A:
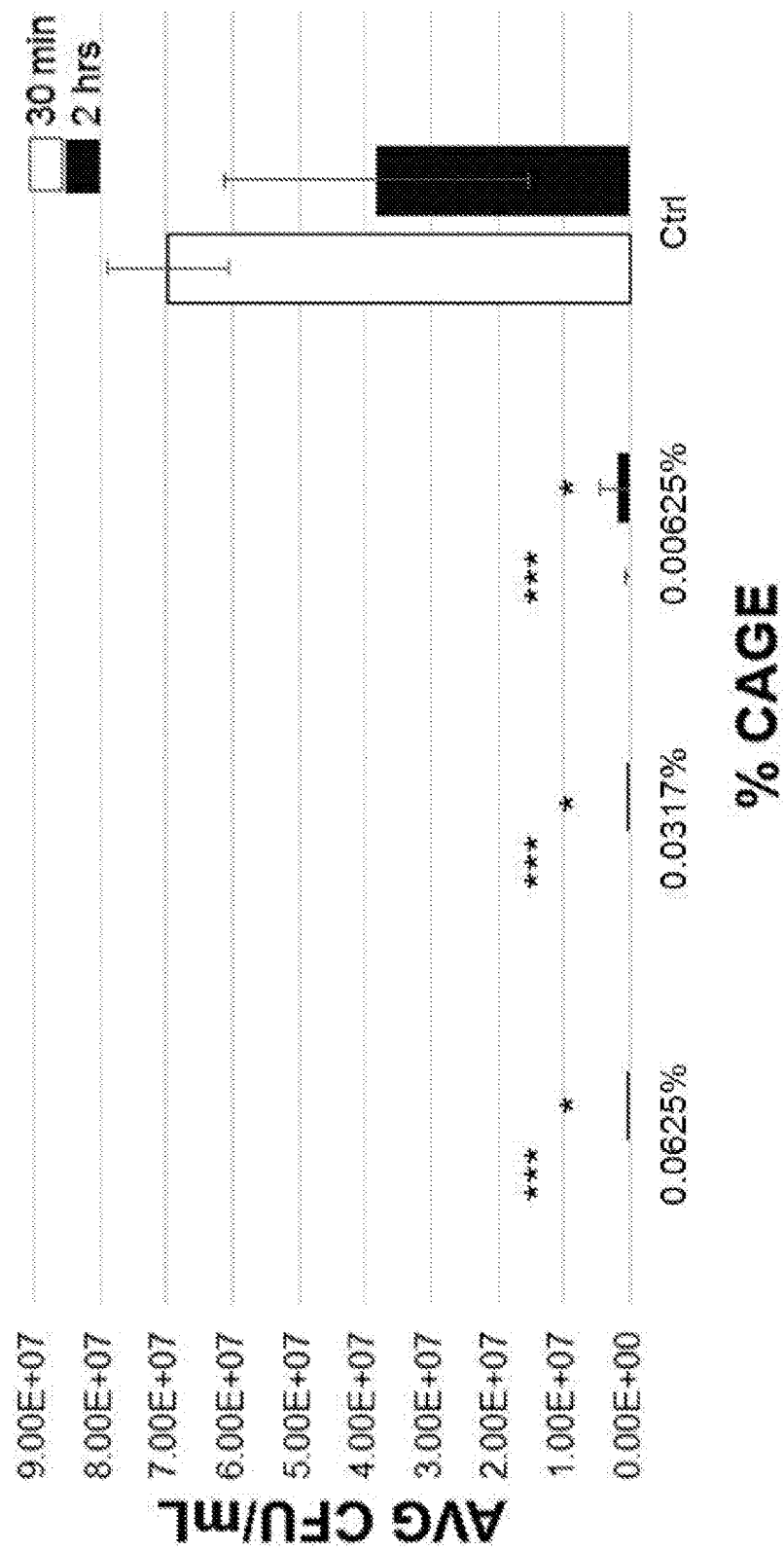
FIG. 9A depicts effects of a particular ionic liquid that includes choline geranate (CAGE) against *P. aeruginosa* on gauze.
Figure 9B:
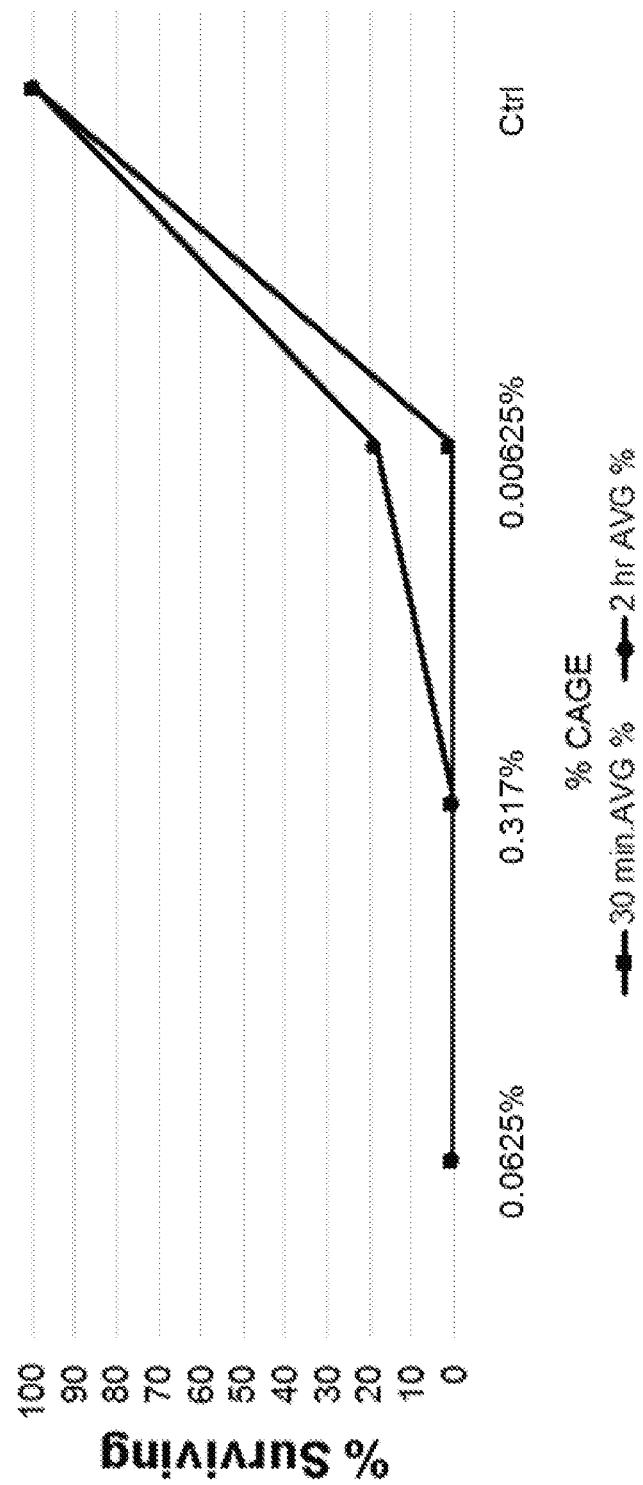
FIG. 9B depicts the percentage of *P. aeruginosa* colonies remaining on the gauze at 30 minutes or two hours following treatment (*=$p<0.05$, =$p<0.01$, *=$p<0.001$).
Figure 10A:
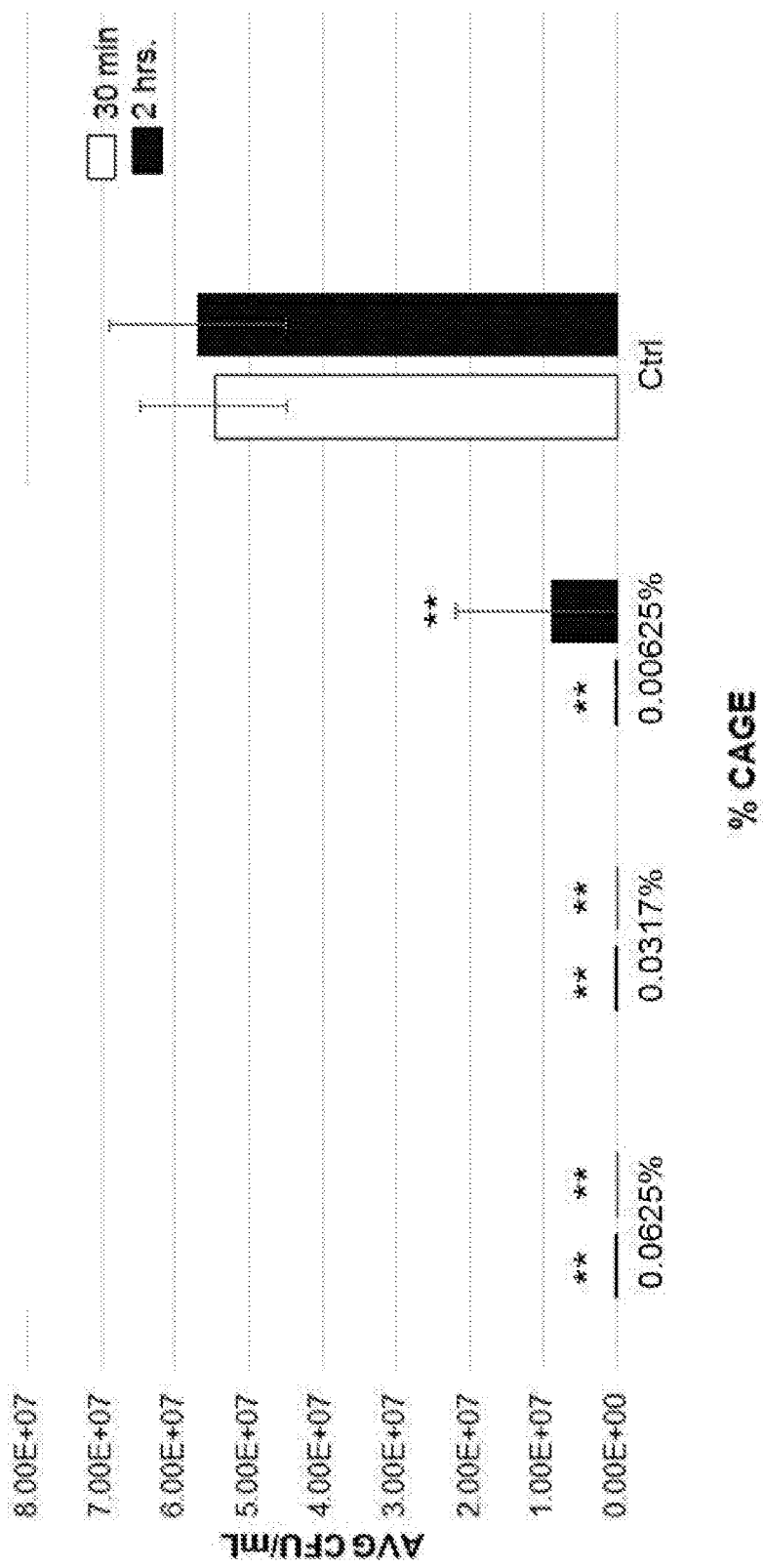
FIG. 10A depicts effects of CAGE against Enterococcus on gauze.
Figure 10B:
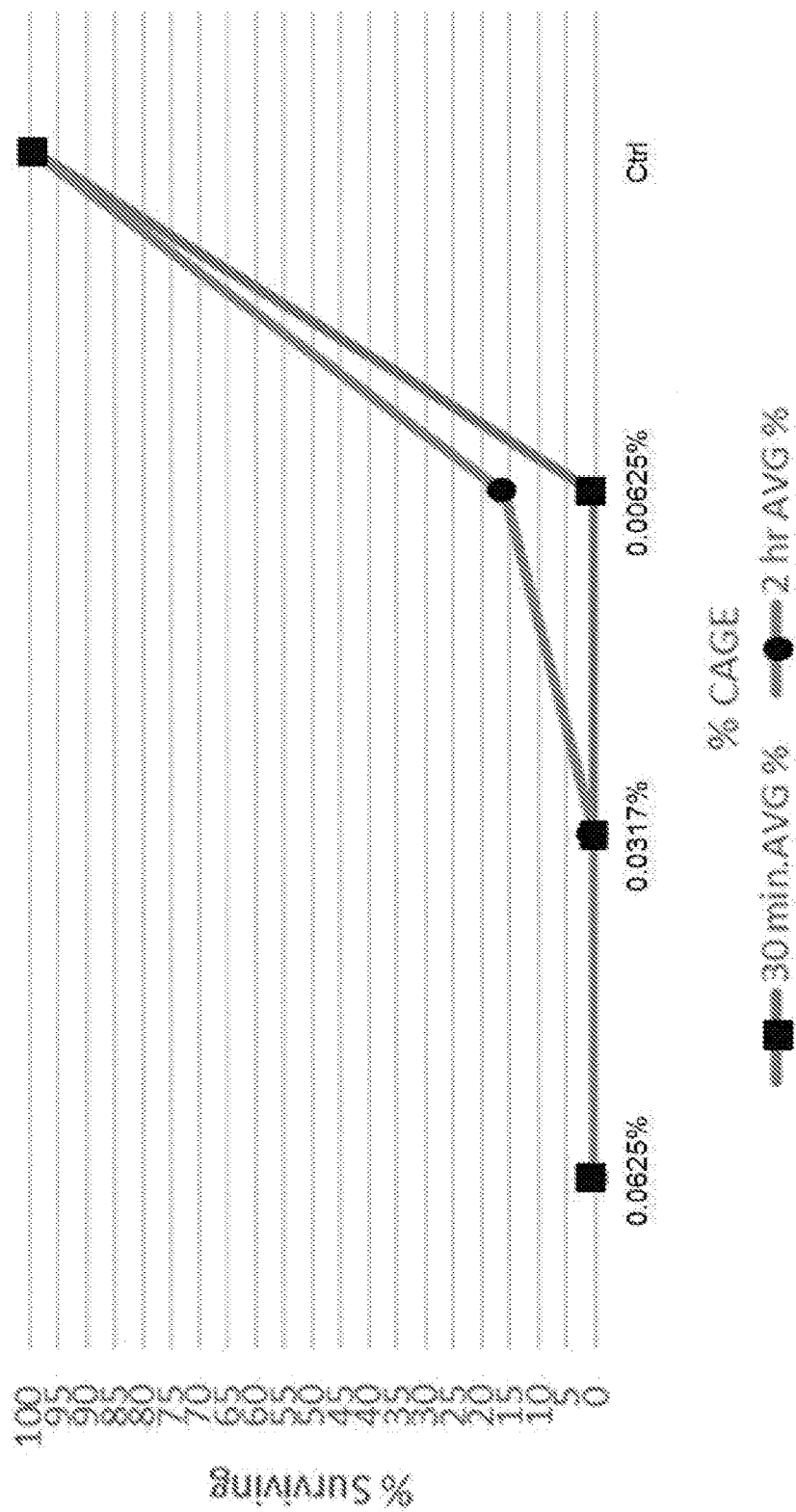
FIG. 10B depicts the percentage of *Enterococcus* colonies remaining on the gauze at 30 minutes or two hours following treatment (*=$p<0.05$, =$p<0.01$, *=$p<0.001$).
Figure 11A:
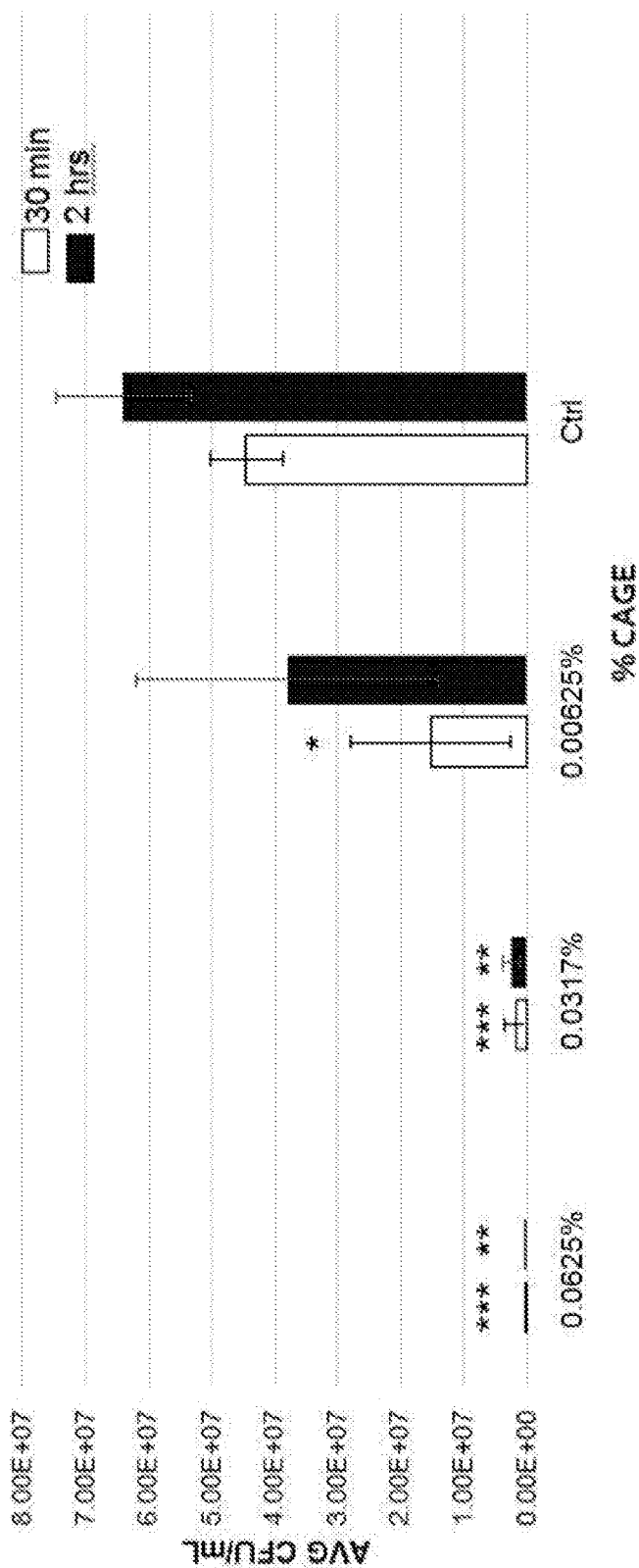
FIG. 11A depicts effects of CAGE against *K. pneumoniae* on gauze.
Figure 11B:
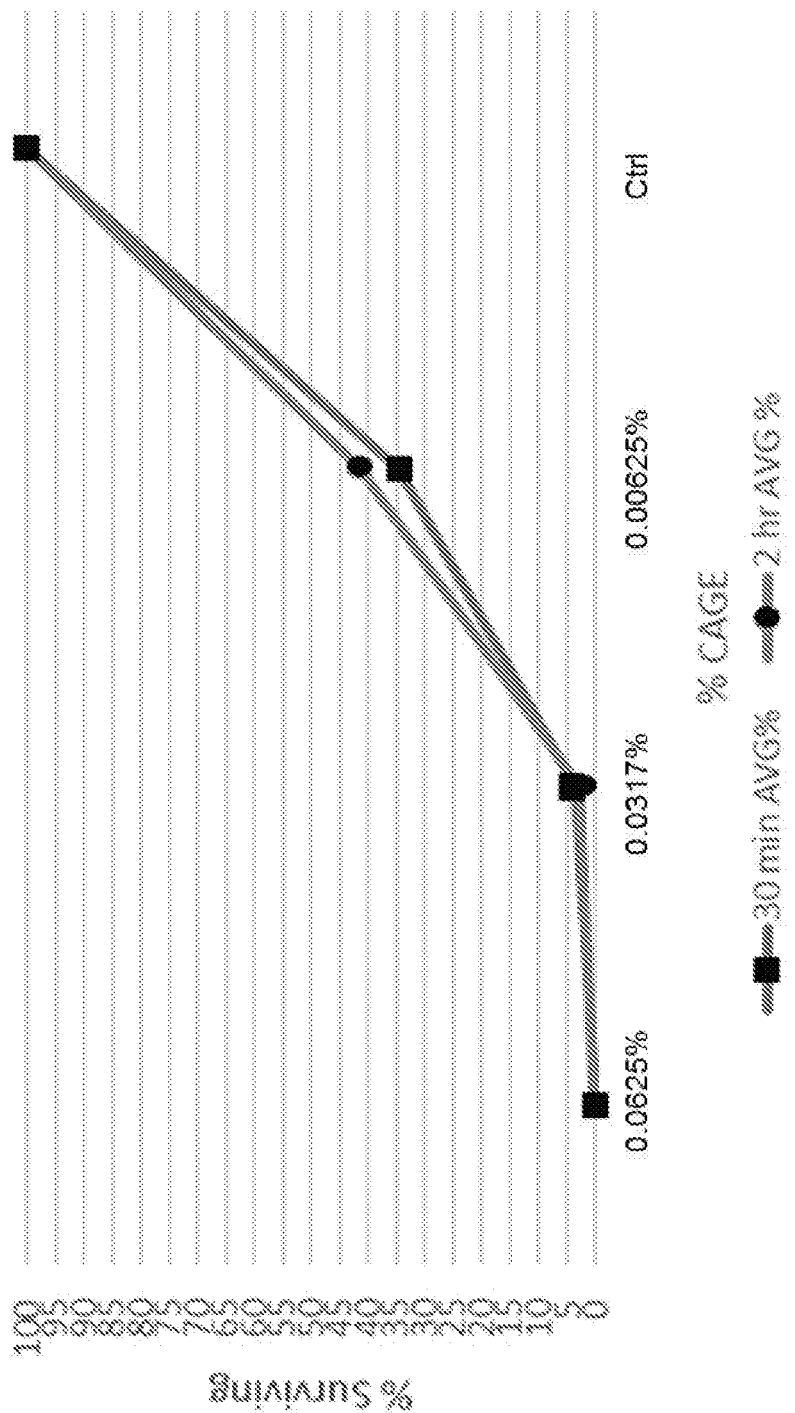
FIG. 11B depicts the percentage of *K. pneumoniae* colonies remaining on the gauze at 30 minutes or two hours following treatment (*=$p<0.05$, =$p<0.01$, *=$p<0.001$).

FIG. 8 shows the $^1$NMR spectrum of the extracted scaffold (top) and authentic CAGE (below) in acetone-d6.

As can be seen in FIG. 8, the spectrum for the extracted scaffold shows characteristic resonances associated with the geranate anion/geranic acid (singlets at ~1.6 and 1.67 ppm, multiplet at 2.0 ppm, singlets at 5.07 and 5.57 ppm) that are similarly observed in the control spectrum. Characteristic resonances of the choline cation are also observed (triplet at 3.85, triplet at 3.42 and singlet at 3.17) in the extracted spectrum, but to a lower molar equivalence than that of the neat CAGE. This is likely due to a relatively inefficient extraction of the choline cation from the scaffold using this particular organic solvent.

Example 3

Efficacy of Ionic Liquid-Incorporated Wound Dressings to Resist Biofouling/Reduce Biofilms The following example demonstrates the efficacy of the IL-incorporated wound care compositions for the reduction of biofilm formation and the prevention and inhibition of pathogen proliferation and growth in wounds.

The effect of the IL-incorporated dressings to either resist or to treat biofilms was quantified using in vitro assays with pathogens associated with skin wounds (e.g. *S. aureus*) or diabetic ulcers (e.g. *P. aeruginosa*). To examine the effect of IL-treatment on the resistance of the dressings to biofouling, small (1 cm$^2$ or less) samples of dressings were placed on a solid nutrient medium and inoculated with actively growing bacteria (10$^5$ cells). This method parallels a commonly employed assay known as the colony biofilm test (Merritt et al. (2005) Growing and analyzing static biofilms. *Current protocols* in microbiology Chapter 1:Unit 1B 1; incorporated by reference herein in its entirety). Biofilms were cultured on dressings with various amounts of deposited CAGE and the number of viable cells existing on these surfaces was determined by initial disruption of the biofilm with sonication, followed by dilution and enumeration of the viable bacteria. Biofilm formation was assayed using culture and qPCR of the bacterial populations as a function of IL concentration and time (24 to 72 hrs). Similarly, the ability of the IL-treated dressings to reduce viability in an established biofilm was assessed by overlaying small pieces of dressing upon biofilms that had been previously cultured on a surface of equivalent size; effectiveness was quantified as a function of treated material and length of exposure.

Example 4

CAGE-Incorporated Wound Dressings

The following example demonstrates the efficacy of CAGE-incorporated gauze for the reduction of biofilm formation and the prevention and inhibition of pathogen proliferation and growth.

Gauze was coated with an IL, CAGE, in various concentrations. The CAGE-incorporated gauze was treated with approximately 100 µL pf actively growing bacteria, including *P. aeruginosa, Enterococcus, K pneumoniae*, or methicillin sensitive *S. aureus* (MSSA), at 10$^8$-10$^9$ cells per mL. Each of these bacteria are clinically isolated pathogens commonly associated with wounds and 10$^8$-10$^9$ cells/mL is a high concentration of live bacteria. In terms of clinical practice, bacterial concentrations in this amount are unlikely to be found, even in cases of septicemia.

As shown in FIGS. 9 through 12, CAGE-incorporated gauze effectively reduced and/or inhibited the growth of bacteria in the gauze. FIGS. 9A and 9B show that the growth of *P. aeruginosa* was prohibited at both 30 minutes and 2 hours following contact with the gauze when CAGE was present in an amount ranging from 1%-10% (1% is 1.25 µg, 5% is 6.25 µg, and 10% is 12.5 µg CAGE). In contrast, control gauze with no IL incorporation showed elevated bacteria amounts. In addition, the percentage of surviving colonies after contact with CAGE-incorporated gauze was reduced to values of less than about 20% in all treatment groups, as compared to percentage of surviving colonies that were untreated.

Figure 12A:
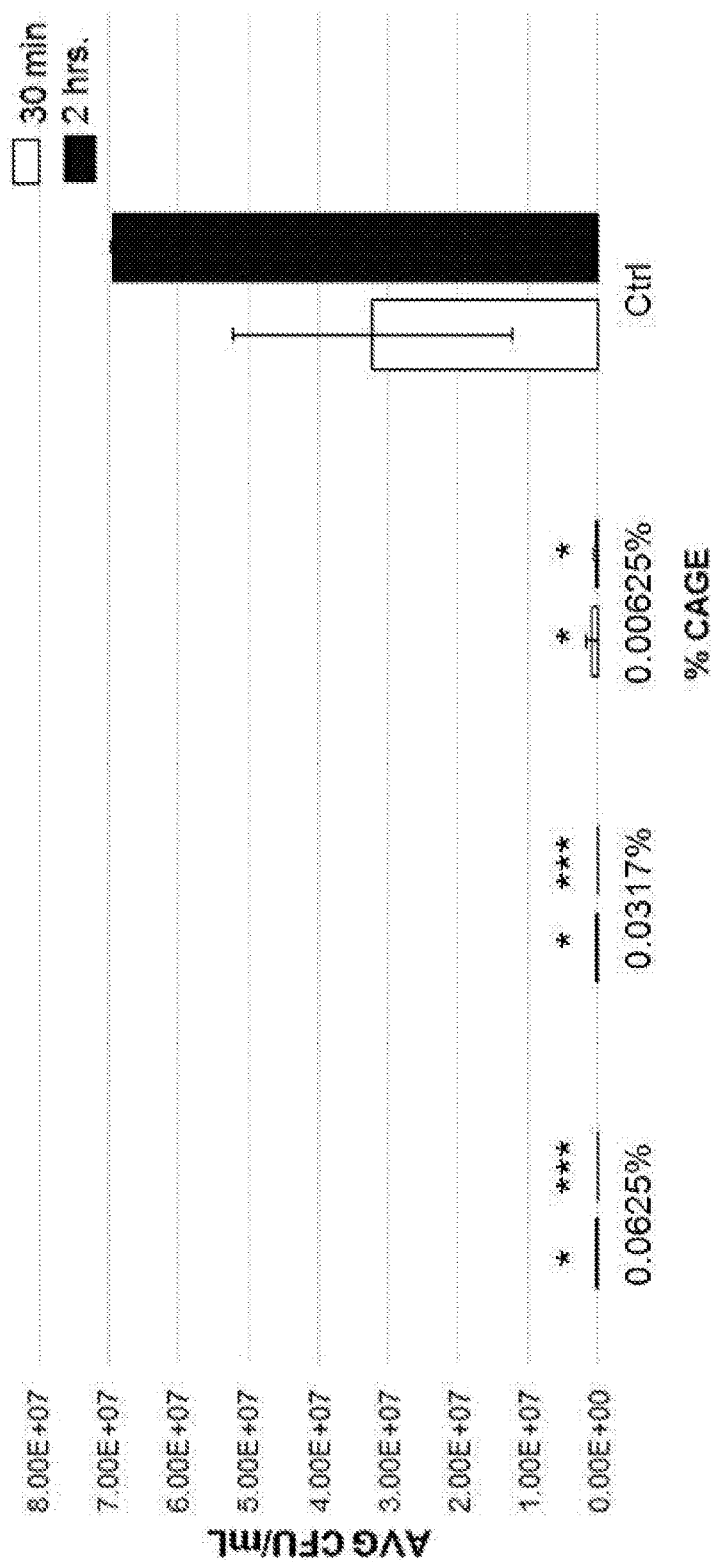
FIG. 12A depicts effects of CAGE against methicillin-sensitive *Staphylococcus aureus* (MSSA) on gauze.
Figure 12B:
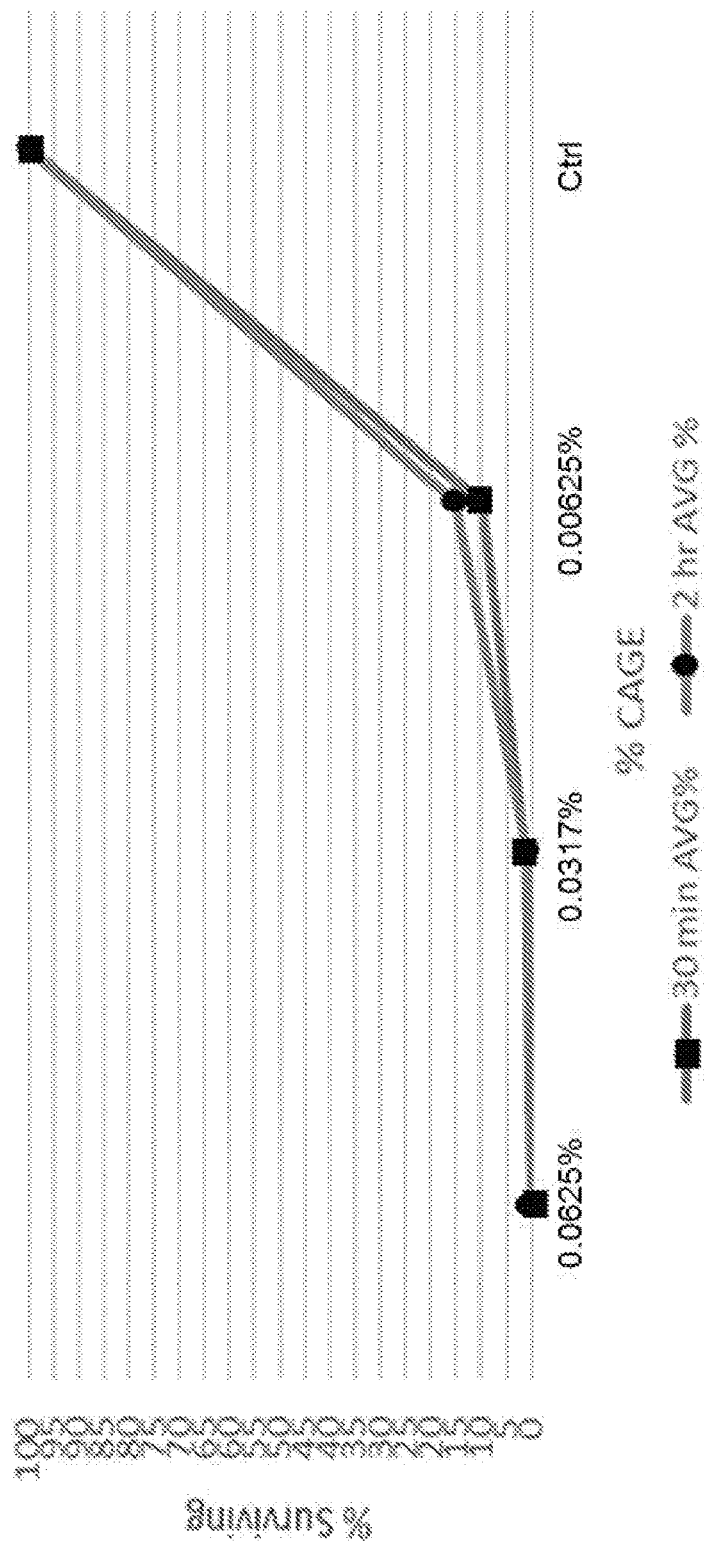
FIG. 12B depicts the percentage of MSSA colonies remaining on the gauze at 30 minutes or two hours following treatment (*=$p<0.05$, =$p<0.01$, *=$p<0.001$).

Similar results are achieved when the gauze is exposed to *Enterococcus* (FIGS. 10A and 10B), *K. pneumoniae* (FIGS. 11A and 11B), and MSSA (FIGS. 12A and 12B).

Example 5

CAGE-Incorporated Scaffolds

The following example demonstrates the efficacy of CAGE-incorporated scaffolds for the reduction of biofilm formation and the prevention and inhibition of pathogen proliferation and growth.

Figure 13A:
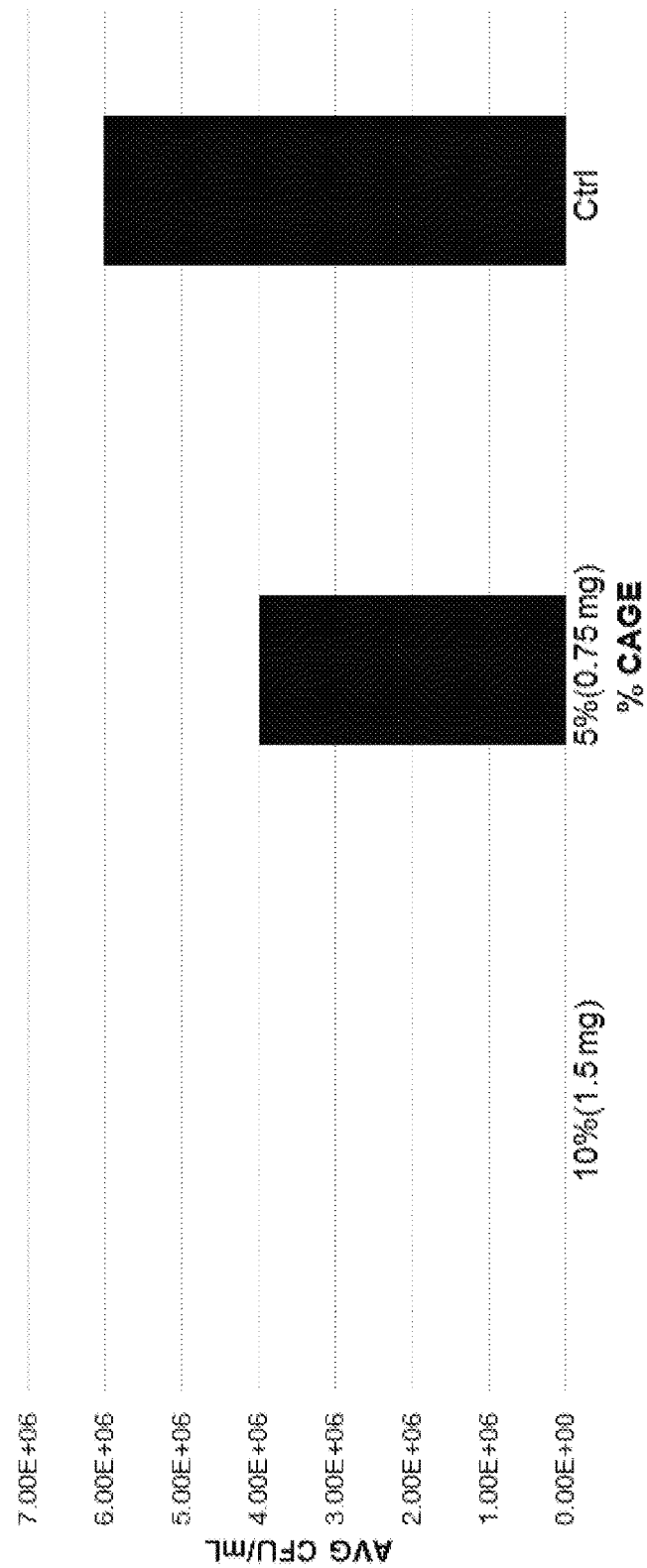
FIGS. 13A and 13B graphically depict the effects of CAGE scaffolds on *P. aeruginosa* at 30 minutes (FIG. 13A) and 2 hours (FIG. 13B) after treatment.
Figure 13B:
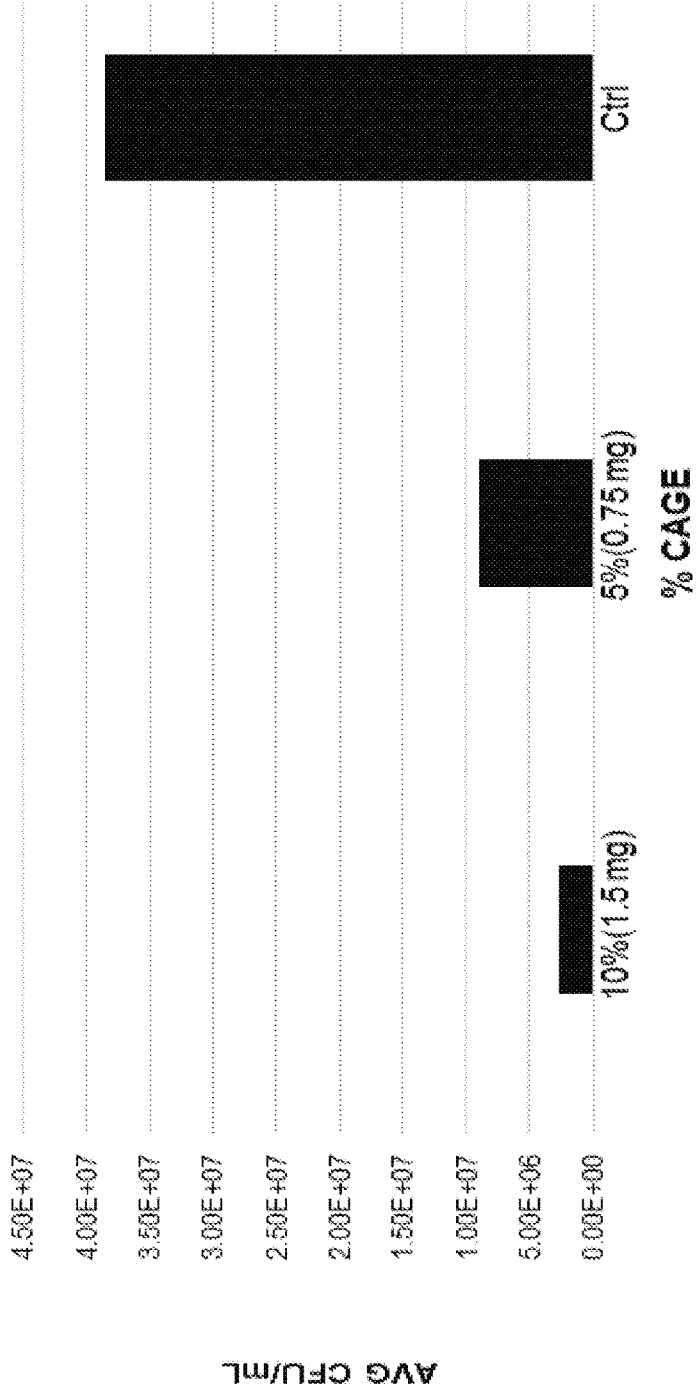

Scaffolds were prepared as described in Example 2, wherein protein was mixed with CAGE to generate a CAGE-incorporated scaffold. The CAGE scaffolds included various concentrations of CAGE from 1% to 10% during the production process (1% is 1.25 µg, 5% is 6.25 µg, and 10% is 12.5 µg CAGE). The CAGE scaffolds were prepared by electrospinning. As shown in FIGS. 13 through 14, CAGE incorporated into protein scaffolds reduced bacteria growth. Specifically, FIGS. 13A and 13B show reduced colony forming units (CFU) of *P. aeruginosa* in CAGE-incorporated scaffolds (at 10% and 5%) compared to control scaffold with no IL incorporation at both 30 minutes and 2 hours after exposure to the bacteria.

Figure 14A:
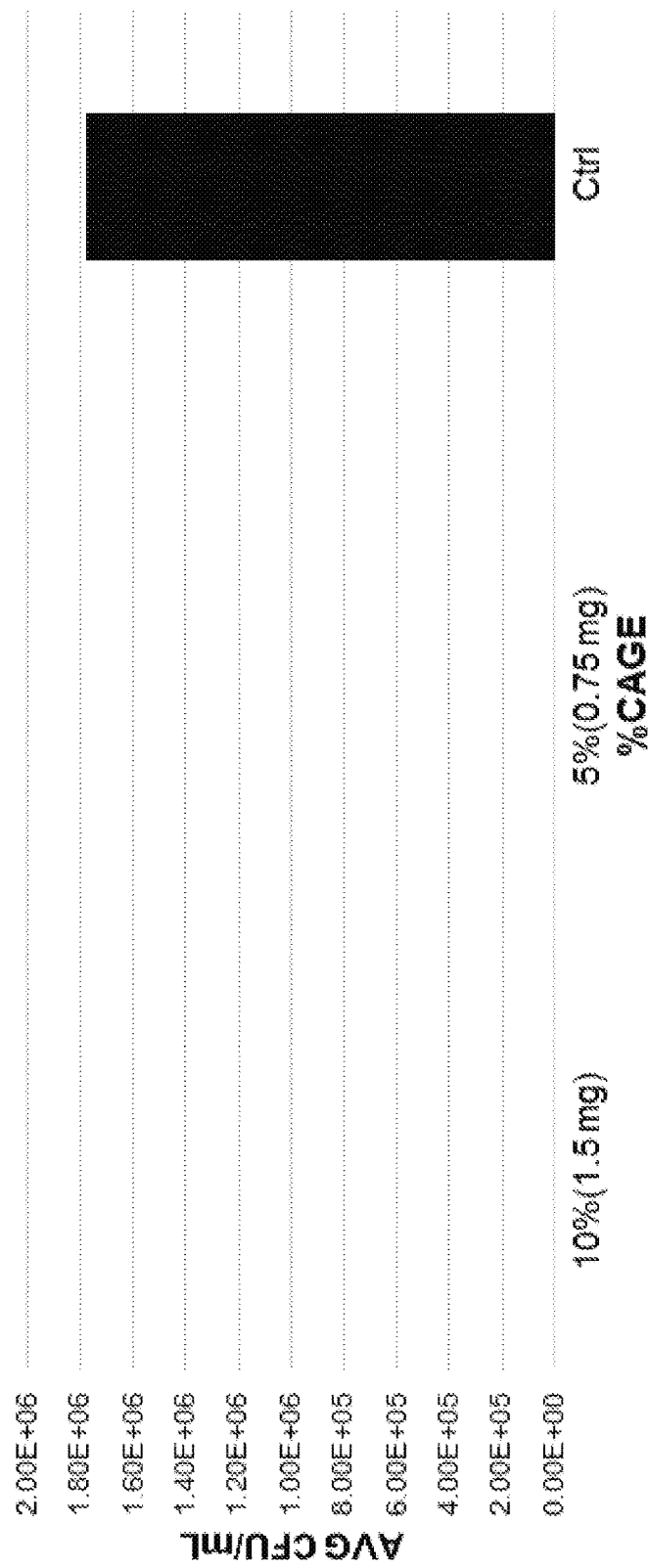
FIGS. 14A and 14B graphically depict the effects of CAGE scaffolds on *Enterococcus* at 30 minutes (FIG. 14A) and 2 hours (FIG. 14B) after treatment.
Figure 14B:
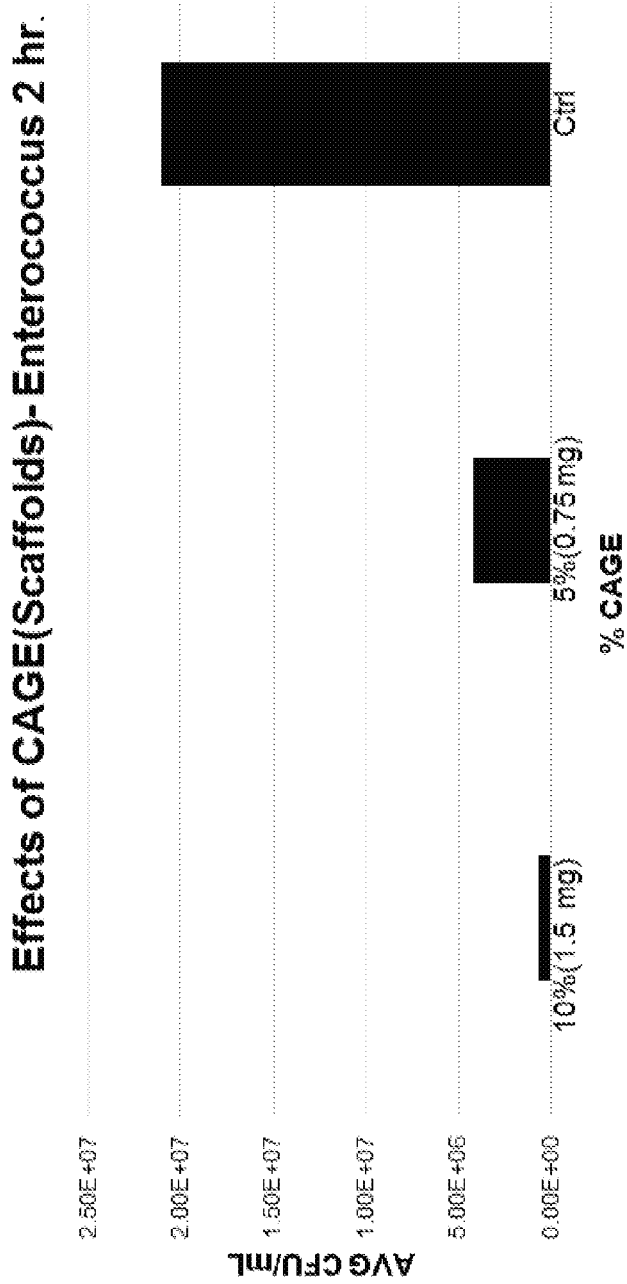

Similarly, FIGS. 14A and 14B show reduced CFU of *Enterococcus* in CAGE-incorporated scaffolds (at 10% and 5%) compared to control scaffold with no IL incorporation at both 30 minutes and 2 hours after exposure to the bacteria.

Figure 15A:
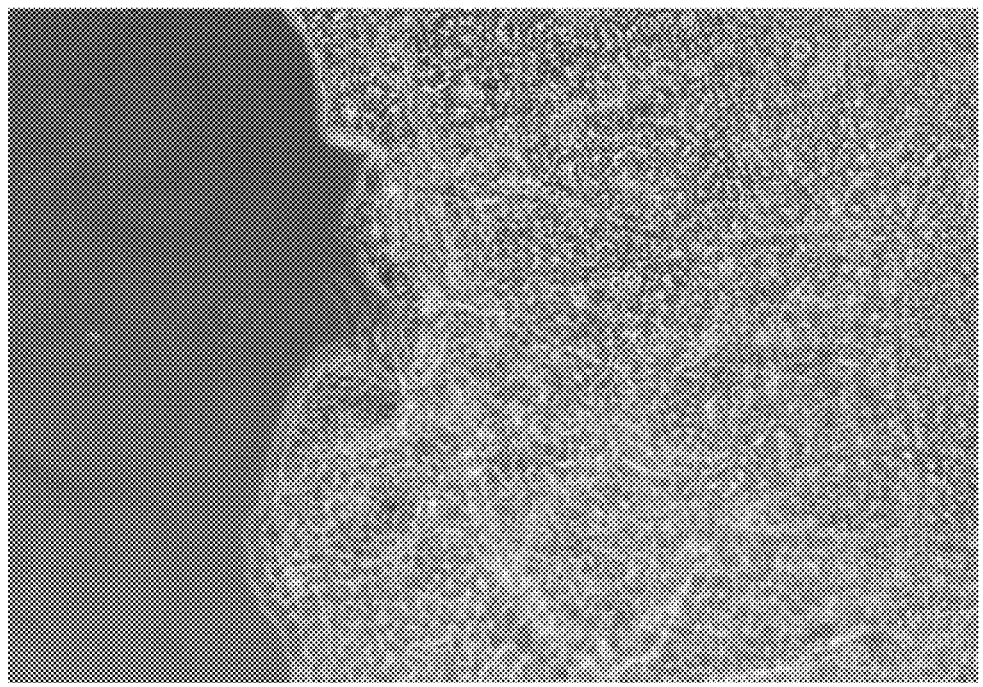
FIGS. 15A and 15B depict micrographs showing human dermal neonatal fibroblasts (P9) on control scaffolds (FIG. 15A) or CAGE-incorporated scaffolds (FIG. 15B).
Figure 15B:
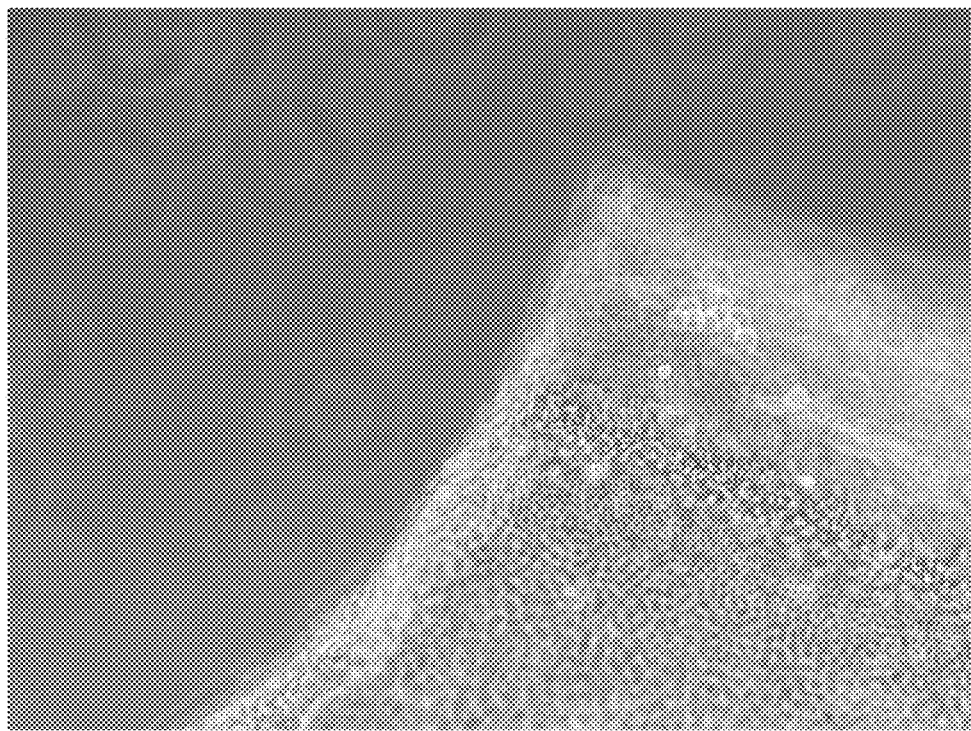

FIGS. 15A and 15B show the ability of human dermal neonatal fibroblasts to attach and proliferate in general growth medium to both the surface of control scaffolds (FIG. 15A) and CAGE-incorporated scaffolds (40%) (FIG. 15B). Human dermal neonatal fibroblasts (P9) were added to a well plate containing control scaffolds or scaffolds containing 40% (v/w) CAGE. The control scaffold was UV sterilized prior to seeding cells. These images show that bacteria may be killed without harming or otherwise preventing human cells from proliferating on the surface.

All headings are for the convenience of the reader and should not be used to limit the meaning of the text that follows the heading, unless so specified.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the claims.

What is claimed is:

1. An electrospun wound care composition, comprising:
  an ionic liquid (IL), wherein the ionic liquid is choline geranate (CAGE), and wherein the ionic liquid is present in an amount of about 0.01% w/w to about 99% w/w; and
  a protein solution comprising gelatin,
  wherein the ionic liquid is electrospun with the protein solution.

2. The wound care composition of claim 1, wherein the wound care composition is incorporated with or impregnated into or coated onto a wound dressing, a bandage, a gauze, a patch, a pad, tape, or a wrap.

3. The wound care composition of claim 1, wherein the ionic liquid is present in an amount of about 40% w/w.

4. The wound care composition of claim 1, wherein the protein solution further comprises collagen, albumin, casein, fibrin, fibroin, keratin, elastin, tropoelastin, or combinations thereof.

5. The wound care composition of claim 1, wherein the protein solution is present in an amount of about 1% w/v to about 20% w/v.

6. The wound care composition of claim 1, wherein the protein solution is present in an amount of about 10% w/v.

7. The wound care composition of claim 1, comprising about 0.2% w/w choline geranate (CAGE) and about 10% w/v gelatin.

8. A wound dressing comprising:
a wound care composition of claim 1; and
a wound dressing material.

9. The wound dressing of claim 8, wherein the wound dressing material is a bandage, a wipe, a sponge, a mesh, a dressing, a gauze, a patch, a pad, tape, or a wrap.

10. The wound dressing of claim 8, wherein the wound care composition is present in an amount of about 0.005% v/w to about 2% v/w.

11. The wound dressing of claim 8, wherein the wound care composition is present in an amount of about 0.625% v/w.

12. The wound dressing of claim 8, wherein the wound care composition is incorporated into or coated onto or impregnated with the wound dressing material.

13. A method of making the wound care composition according to claim 1 comprising an ionic liquid (IL) and a protein solution, the method comprising: providing a protein solution comprising gelatin; providing an ionic liquid, wherein the ionic liquid is choline geranate (CAGE); mixing the ionic liquid with the protein solution; and electrospinning the mixture of ionic liquid and protein solution.

14. The method of claim 13, wherein the protein solution comprises collagen, albumin, casein, fibrin, fibroin, keratin, elastin, tropoelastin, or combinations thereof in a solvent.

15. The method of claim 14, wherein the solvent is the ionic liquid or an organic solvent.

16. The method of claim 15, wherein the organic solvent is hexafluoro-2-propanol (HFIP).

17. The method of claim 13, wherein the mixing is performed at a temperature of about 5° C. to about 100° C.

18. The method of claim 13, wherein the electrospinning is performed at a temperature of about 5° C. to about 100° C.

19. The method of claim 13, wherein the electrospinning is performed at a voltage of about 10V to about 50V.

20. The method of claim 13, wherein the electro spinning is performed at a flow rate of about 0.1 mL/hr to about 5 mL/hr.

21. The method of claim 13, wherein the electro spinning is performed at a flow rate of about 1 mL/hr.

22. The method of claim 13, further comprising desiccating the electrospun material to dryness.

* * * * *